(12) United States Patent
Donlan et al.

(10) Patent No.: US 9,457,132 B2
(45) Date of Patent: Oct. 4, 2016

(54) CONTROLLED COVALENT ATTACHMENT OF BIOACTIVE BACTERIOPHAGE FOR REGULATING BIOFILM DEVELOPMENT

(75) Inventors: Rodney Martin Donlan, Atlanta, GA (US); Susan Marie Lehman, Atlanta, GA (US); Andres J. Garcia, Atlanta, GA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 159 days.

(21) Appl. No.: 14/119,716

(22) PCT Filed: Jun. 28, 2012

(86) PCT No.: PCT/US2012/044707
§ 371 (c)(1),
(2), (4) Date: Mar. 6, 2014

(87) PCT Pub. No.: WO2013/048604
PCT Pub. Date: Apr. 4, 2013

(65) Prior Publication Data
US 2014/0199360 A1     Jul. 17, 2014

Related U.S. Application Data

(60) Provisional application No. 61/501,975, filed on Jun. 28, 2011.

(51) Int. Cl.
| | |
|---|---|
| *A61L 29/10* | (2006.01) |
| *A01N 63/00* | (2006.01) |
| *A61L 27/34* | (2006.01) |
| *A61L 27/52* | (2006.01) |
| *A61L 27/54* | (2006.01) |
| *A61L 29/08* | (2006.01) |
| *A61L 29/14* | (2006.01) |
| *A61L 31/10* | (2006.01) |
| *A61L 31/14* | (2006.01) |
| *A61L 31/16* | (2006.01) |
| *A61L 15/60* | (2006.01) |
| *A61L 15/36* | (2006.01) |
| *A61L 27/36* | (2006.01) |
| *A61L 29/16* | (2006.01) |
| *A61L 15/44* | (2006.01) |
| *A61K 35/76* | (2015.01) |
| *A61M 25/00* | (2006.01) |

(52) U.S. Cl.
CPC ............ *A61L 29/106* (2013.01); *A01N 63/00* (2013.01); *A61L 15/36* (2013.01); *A61L 15/44* (2013.01); *A61L 15/60* (2013.01); *A61L 27/34* (2013.01); *A61L 27/3637* (2013.01); *A61L 27/52* (2013.01); *A61L 27/54* (2013.01); *A61L 29/08* (2013.01); *A61L 29/085* (2013.01); *A61L 29/145* (2013.01); *A61L 29/16* (2013.01); *A61L 31/10* (2013.01); *A61L 31/145* (2013.01); *A61L 31/16* (2013.01); *A61K 35/76* (2013.01); *A61L 2300/102* (2013.01); *A61L 2300/104* (2013.01); *A61L 2300/404* (2013.01); *A61L 2300/406* (2013.01); *A61L 2300/606* (2013.01); *A61M 2025/0056* (2013.01); *C12N 2795/10132* (2013.01); *C12N 2795/10232* (2013.01); *C12N 2795/10332* (2013.01)

(58) Field of Classification Search
CPC ...... A01N 63/00; A01N 25/10; A01N 25/34; A61K 35/76; A61L 2300/102; A61L 2300/104; A61L 2300/404; A61L 2300/406; A61L 2300/606; A61L 27/34; A61L 27/3637; A61L 27/52; A61L 27/54; A61L 29/08; A61L 29/085; A61L 29/106
See application file for complete search history.

(56) References Cited

U.S. PATENT DOCUMENTS

| | | | |
|---|---|---|---|
| 6,110,483 A | 8/2000 | Whitbourne et al. | |
| 6,579,539 B2 | 6/2003 | Lawson et al. | |
| 2002/0127547 A1 | 9/2002 | Miller | |
| 2005/0220770 A1* | 10/2005 | Scott et al. | 424/93.6 |
| 2009/0130196 A1 | 5/2009 | Murthy et al. | |
| 2009/0191254 A1 | 7/2009 | Curtin et al. | |

FOREIGN PATENT DOCUMENTS

| | | |
|---|---|---|
| EP | 1496919 A2 | 1/2005 |
| WO | WO-2005009451 A1 | 2/2005 |

OTHER PUBLICATIONS

Donlan, Rodney M., "Preventing biofilms of clinically relevant organisms using bacteriophage," vol. 17, No. 2, pp. 66-72, Jan. 21, 2009.
International Search Report and Written Opinion for co-pending application Serial No. PCT/US2012/044707, issued Apr. 23, 2013.

* cited by examiner

*Primary Examiner* — Sue Liu
*Assistant Examiner* — Thor Nielsen
(74) *Attorney, Agent, or Firm* — Dinsmore & Shohl LLP; Weston R. Gould

(57) ABSTRACT

Medical devices that are resistant to biofilm development and methods of the manufacture of biofilm resistant medical devices are provided. One or more bacteriophages are tethered to the surface of a medical device or a hydrogei-type coating on the surface of the device by covalent bonding while maintaining bacteriophage infective or lytic activity. The presence of the bacteriophages on a medical device, such as an indwelling medical device, prevents biofilm formation or reduces existing biofilm formation on the surface of the device when in use. These devices address the long felt need for biofilm resistant devices that increase safety and reduce complications normally associated with prior indwelling or other medical devices.

19 Claims, 12 Drawing Sheets

CONTROLLED COVALENT ATTACHMENT OF BIOACTIVE BACTERIOPHAGE FOR REGULATING BIOFILM DEVELOPMENT

CROSS REFERENCE TO RELATED APPLICATIONS

This application is the U.S. national phase of PCT/US2012/044707 filed Jun. 28, 2012, which claims priority to U.S. Provisional Application No. 61/501,975 filed Jun. 28, 2012, the entire contents of which are incorporated herein by reference.

GOVERNMENT INTEREST

The invention described herein may be manufactured, used, and licensed by or for the United States Government.

FIELD OF THE INVENTION

Methods for production of covalently bound bioactive bacteriophage(s) to surfaces for the prevention or amelioration of biofilm formation are provided. The methods are useful for the production of medical devices such as indwelling catheters and the prevention or treatment of biofilm formation or localized bacterial infections.

BACKGROUND OF THE INVENTION

According to the US Department of Health and Human Services, healthcare-associated infections (HAI), such as catheter-associated bloodstream and urinary tract infections, ventilator-associated pneumonia, and surgical site infections, are among the leading causes of hospital deaths in the US, accounting for 1.7 million infections and 99,000 associated deaths in 2002. [1,2] Treating HAI translates to increases in the cost of patient care. For example, it is estimated that HAI incur an estimated $28-33 billion in excess healthcare costs each year [1]. Catheter-associated urinary tract infections (CAUTI) are the most common HAI, representing more than 30% of HAI reported by acute care hospitals [3]. This translates into >560,000 infections annually, with an attributable mortality rate of 2.3% (>13,000 deaths) [3]. In addition to UTI-attributable deaths, CAUTI are the leading cause of secondary healthcare-associated bloodstream infections, which have a mortality rate of 10% [4]. Overall, CAUTI significantly increase patient morbidity, increasing hospital stays and costs of patient care [5-8]. Catheter-associated microbes are also thought to be one of the largest reservoirs of nosocomial antibiotic-resistant pathogens [9, 10].

Most CAUTI develop when bacteria from a variety of sources colonize the urinary catheter [11-13]. Upon attaching to surfaces of the device, bacteria proliferate and form aggregates within a complex matrix consisting of extracellular polymeric substances, typically polysaccharides and polypeptides [15]. This mass of attached bacteria and the associated extracellular polymeric substances is commonly referred to as a biofilm or slime [63]. Antibacterial agents have difficulty penetrating biofilms and killing and/or inhibiting the proliferation of the bacteria within the biofilm [64]. The colonization of the bacteria on and around the device and the synthesis of the biofilm barrier may eventually result in encrustation, occlusion and failure of the device. The biofilm itself also serves as a sanctuary for pathogens, particularly bacterial pathogens including gram positive bacteria (such a *Staphylococcus* species and *Enterococcus* species), and gram negative bacteria (such as *Enterobacter* species and *Pseudomonas* species).

Biofilm-associated organisms may elicit disease processes by detachment of individual cells or aggregates of cells resulting in bloodstream or urinary tract infections, by production of endotoxin, or by providing a niche for the development of antimicrobial-resistant organisms. One example of a pathogen associated with CAUTI is *Staphylococcus aureus*. Both *S. aureus* and coagulase-negative staphylococci (for example, *S. epidermidis*) have emerged as major nosocomial pathogens associated with biofilm formation on implanted medical devices [65;66]. These organisms are among the normal carriage flora of human skin and mucous membranes, making them prevalent complications during and after invasive surgery or prolonged hospital stays. As bacteria carried on both healthy and sick people, staphylococci are considered opportunistic pathogens that invade subjects via open wounds and via implanted medical devices.

Several approaches for delaying CAUTI biofilm development have been investigated but no effective strategy has been established. Because biofilm organisms are highly tolerant to antimicrobial agents, infections associated with indwelling catheters often do not respond to systemic drug therapy. Instillation of the catheter retention balloon with bactericidal chemicals may introduce high enough local concentrations to significantly inhibit biofilm formation, but only certain combinations of chemicals and catheter materials are compatible [18,19]. Catheter coatings impregnated with silver alloy have shown mixed results with no clear efficacy in human patients [20-22]. Prior methods designed to impregnate bacteriophage failed to produce sufficient reduction in biofilm formation.

Therefore, there is a need for new methods of preventing or treating biofilm formation on the surface of medical devices, or for localized therapy of bacterial infection such as in burn therapy.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

A medical device is provided that is suitable for short or long term indwelling or surface use for a subject that is resistant to biofilm development by the inclusion of one or more bioactive bacteriophages covalently tethered to one or more surfaces of the device. A medical device includes one or more surfaces; and a bioactive bacteriophage composition covalently tethered to the surface or a coating material carried by one or more of the surfaces, wherein the bacteriophage are not embedded into the coating or the surface, and wherein the bacteriophage composition is capable of inhibiting formation of bacterial biofilm on the medical device. Medical devices claimed are capable of being used for short or long term applications and continue to prevent biofilm formation on the device while in use.

Also provided is a method for inhibiting formation of a bacterial biofilm on a surface of a medical device including covalently tethering one or more bacteriophages that inhibit formation of a bacterial biofilm to the surface of a medical device, or a coating material present on a surface of a medical device, prior to formation of a biofilm on the surface or coating. Alternatively, a bacteriophage is tethered to a device either on a surface or a coating on the surface following some level of biofilm formation whereby the tethered phage is capable of reducing the biofilm presence or preventing further biofilm formation.

Methods of forming a medical device are also provided that include covalently tethering a bioactive bacteriophage into a coating material on one or more surfaces of a medical device. Methods optionally include activating a surface or coating material on a medical device with 4-nitrophenyl chloroformate, or other suitable tethering chemistry, to produce an activated surface prior to covalently tethering a bacteriophage.

The devices and methods provided prevent or treat biofilm formation on the surface of a medical device, improve medical device functionality, reduce complications of medical device use, and/or improve subject compliance.

DETAILED DESCRIPTION OF EMBODIMENTS OF THE INVENTION

Figure 1A:
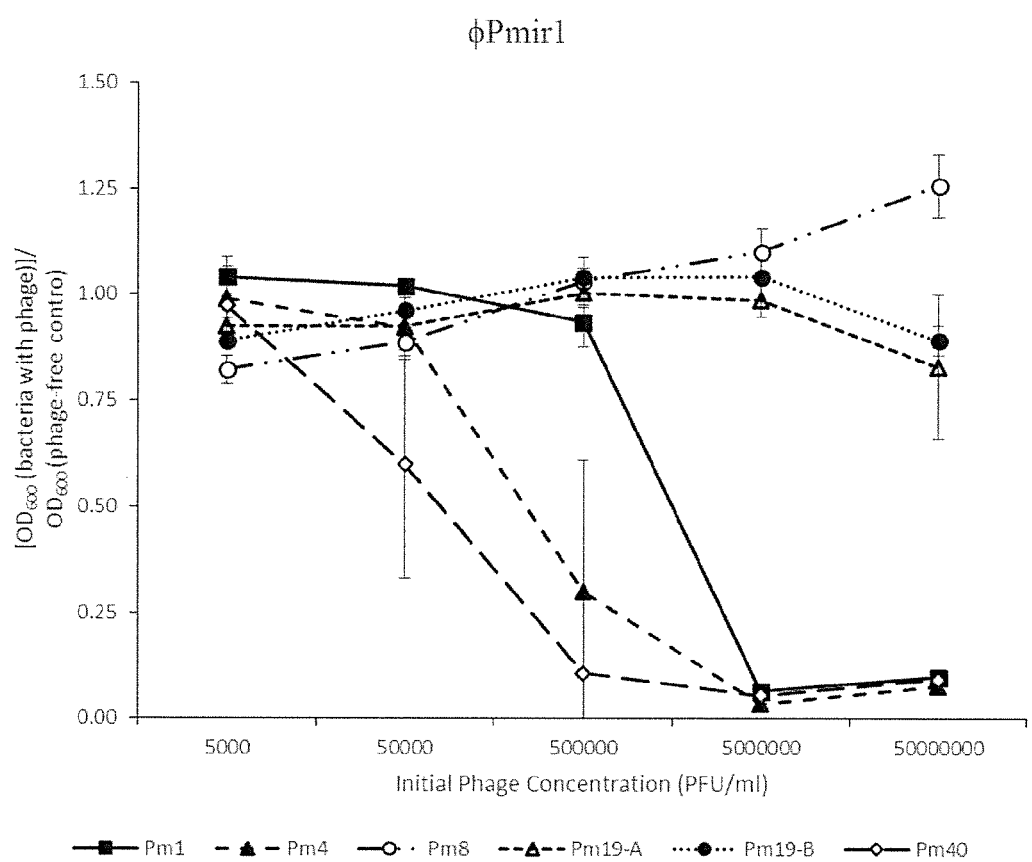
FIG. 1A illustrates the ability of phage ΦPmir1 to inhibit growth of *Pr. mirabilis*.
Figure 1B:
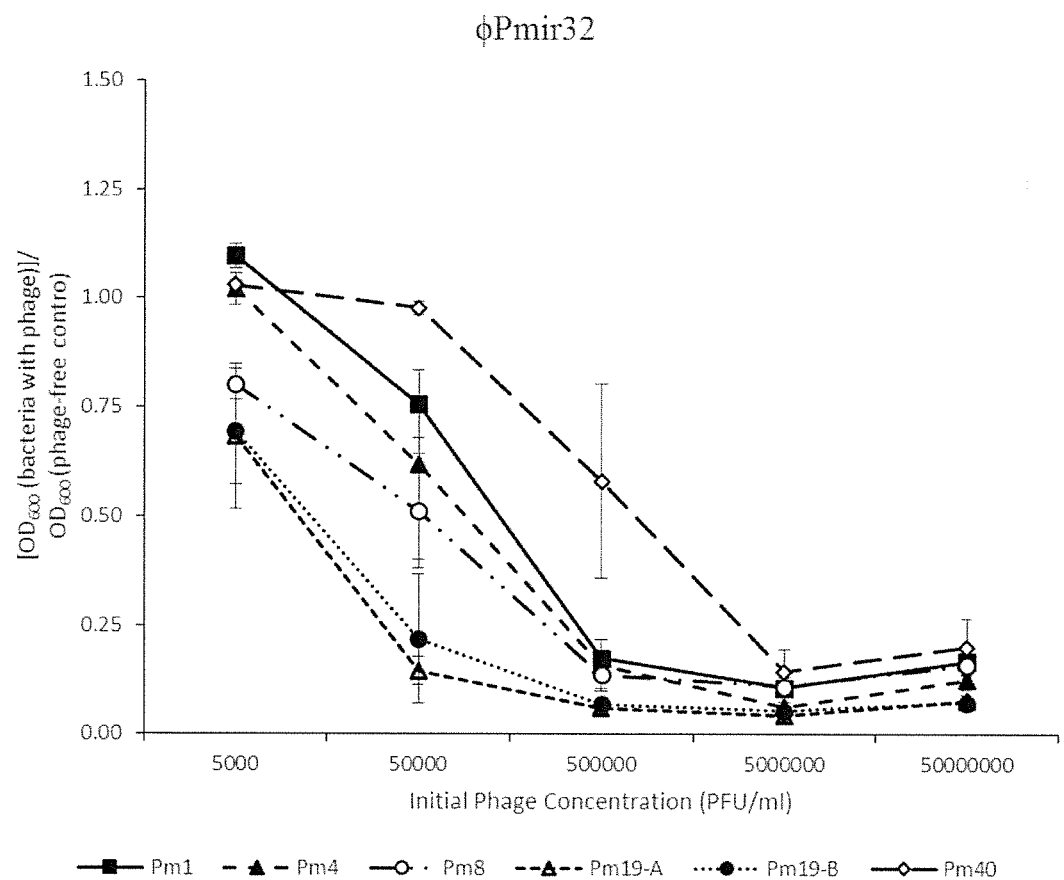
FIG. 1B illustrates the ability of phage ΦPmir32 to inhibit growth of *Pr. mirabilis*.
Figure 1C:
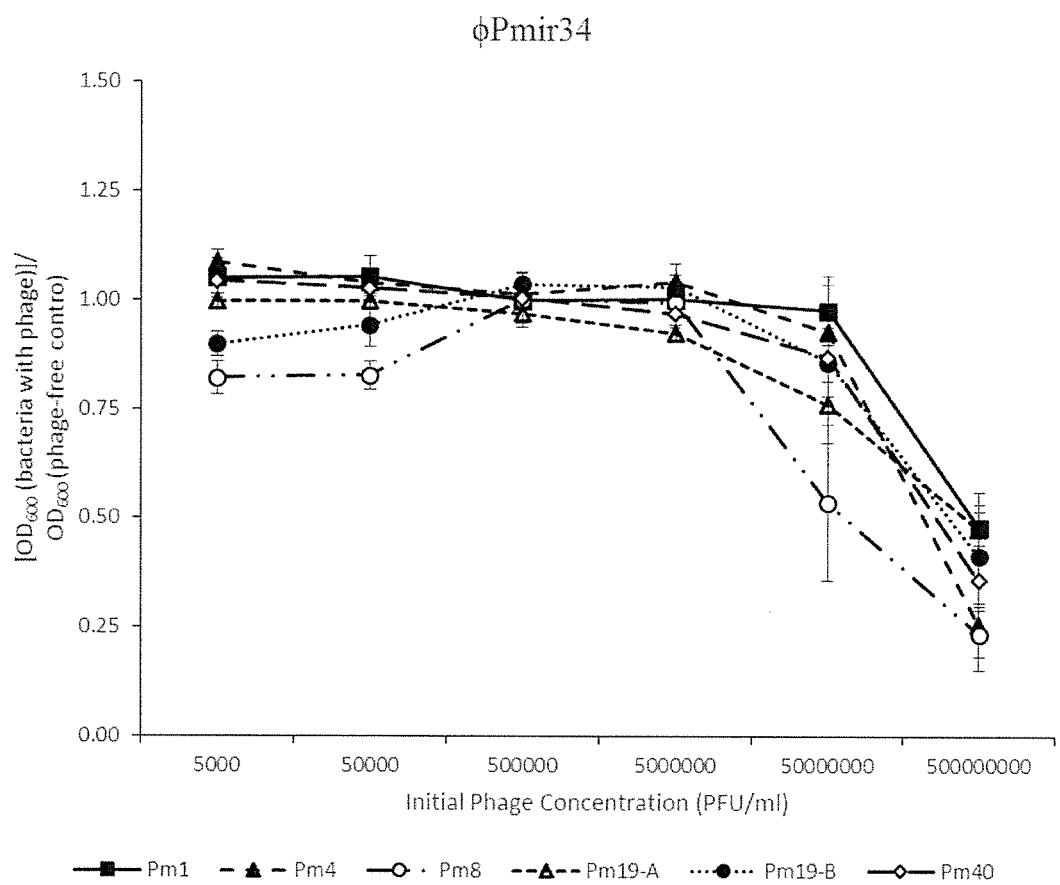
FIG. 1C illustrates the ability of phage ΦPmir34 to inhibit growth of *Pr. mirabilis*.
Figure 1D:
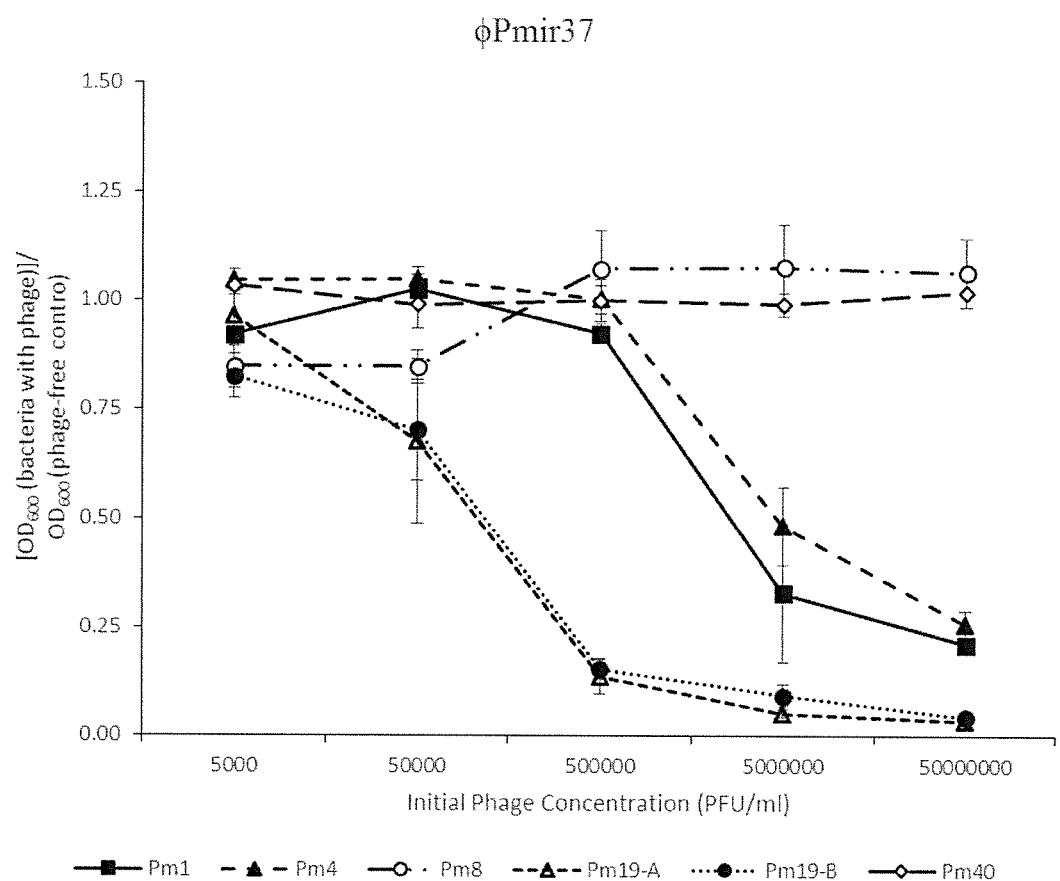
FIG. 1D illustrates the ability of phage ΦPmir37 to inhibit growth of *Pr. mirabilis*.
Figure 2A:
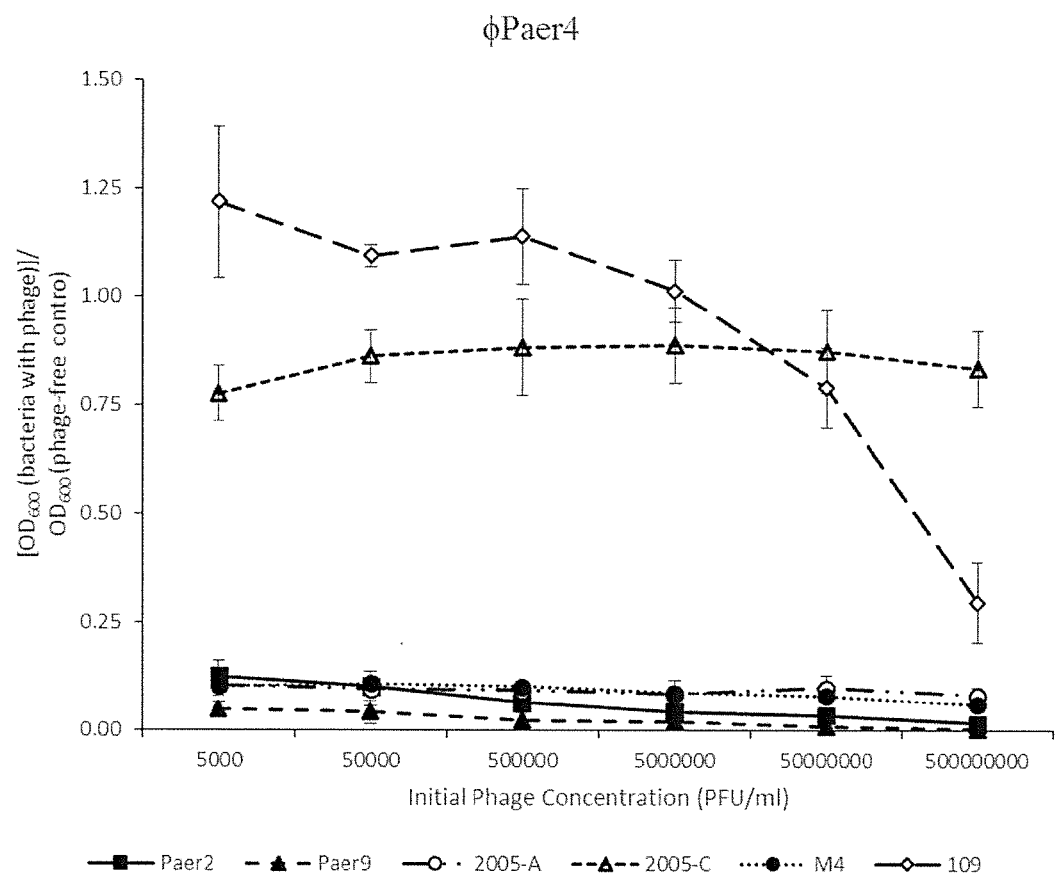
FIG. 2A illustrates the ability of phage ΦPaer4 to inhibit growth of *Ps. aeruginosa*.
Figure 2B:
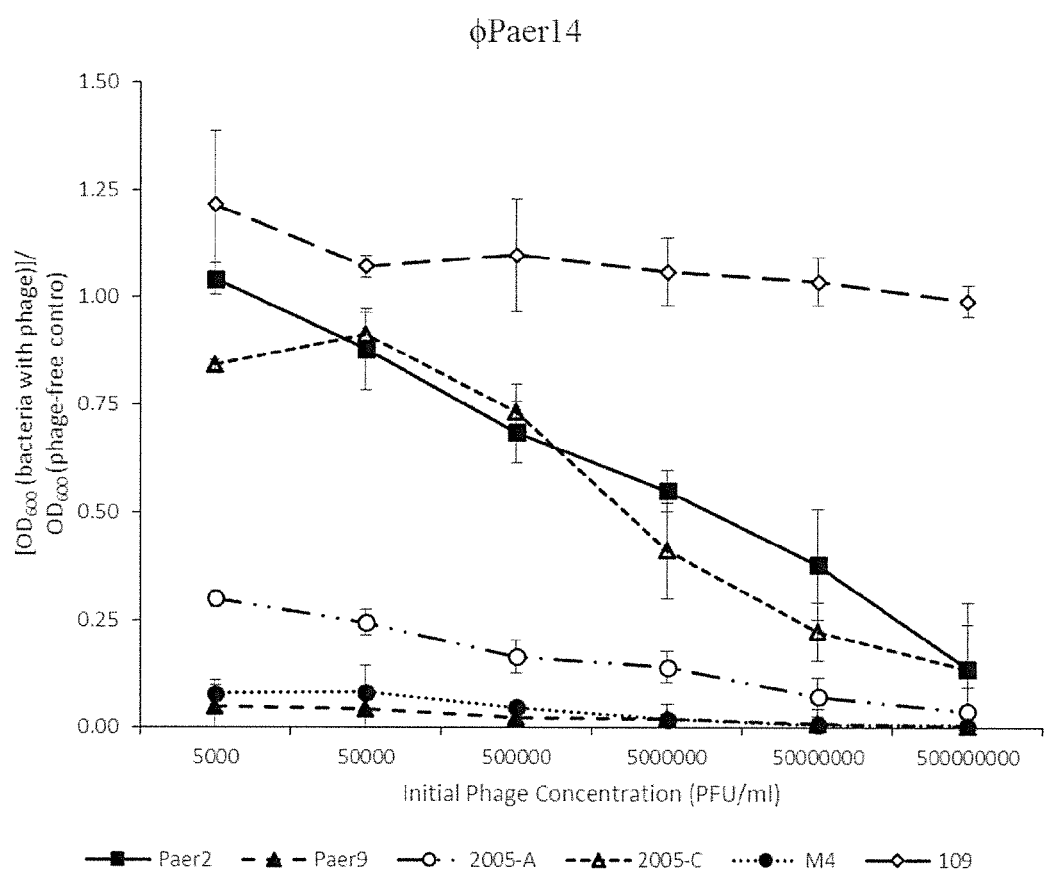
FIG. 2B illustrates the ability of phage ΦPaer14 to inhibit growth of *Ps. aeruginosa*.
Figure 2C:
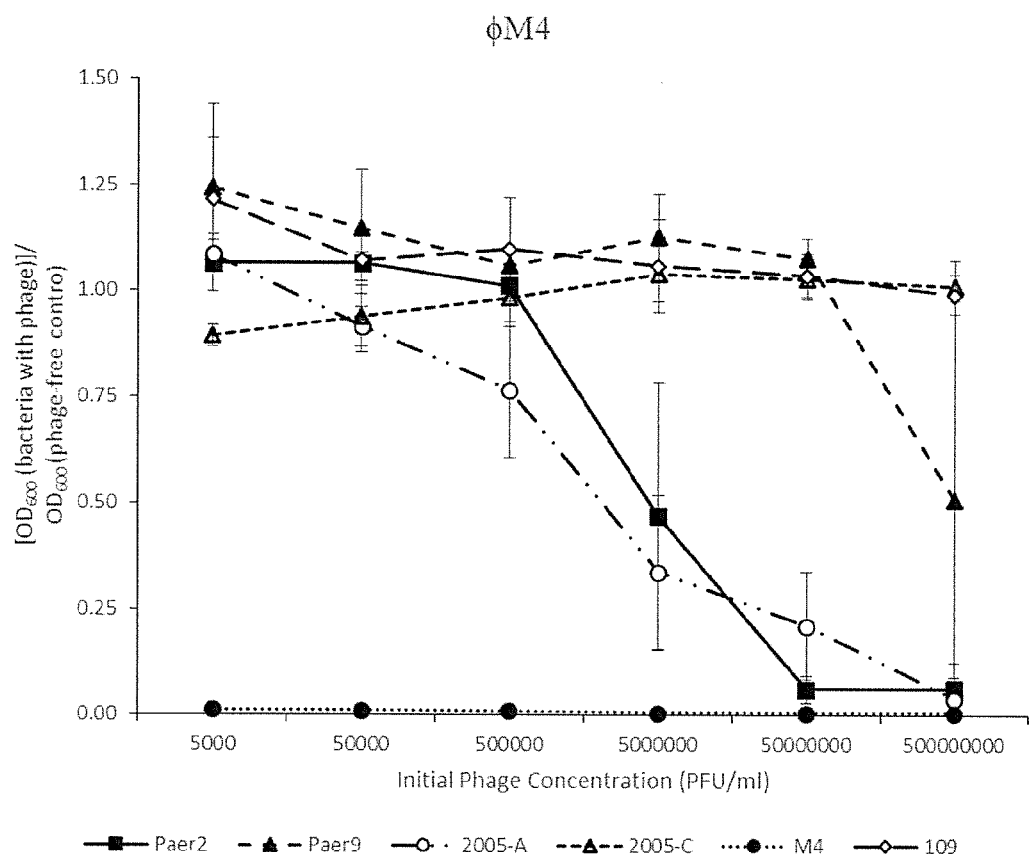
FIG. 2C illustrates the ability of phage ΦM4 to inhibit growth of *Ps. aeruginosa*.
Figure 2D:
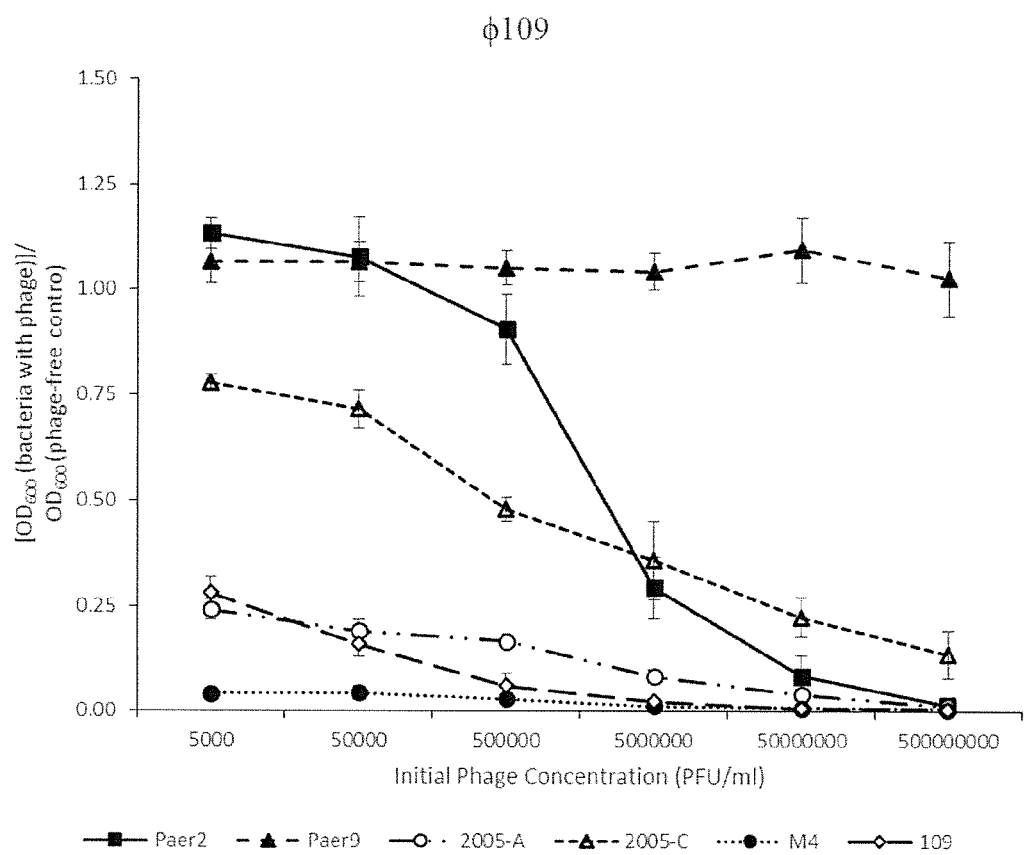
FIG. 2D illustrates the ability of phage Φ109 to inhibit growth of *Ps. aeruginosa*.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the devices and processes are described as an order of individual steps or using specific materials, it is appreciated that described steps or materials may be interchangeable such that the description of the invention includes multiple parts or steps arranged in many ways as is readily appreciated by one of skill in the art.

Methods for the selective association of bioactive bacteriophage (phage) to the surface of a medical device are provided. These methods allow the production of devices that are highly resistant to biofilm formation. Devices such as flexible patches incorporating covalently surface bound bacteriophage are also useful for localized prevention or therapy of bacterial infection. Thus, the invention has utility as for the prevention or treatment of localized bacterial infection and the production of biofilm resistant medical devices.

As used herein the term "bioactive" is intended to mean that a phage tethered to a surface maintains some level of activity of that of an unbound phage. In some embodiments, a tethered phage is bioactive if it is capable of recognizing a target bacterium, binding to a target bacterium, transferring genetic material to a target bacterium, or causing lysis of a target bacterium, or combinations thereof. An "effective amount" of bacteriophage is an amount of bioactive bacteriophage sufficient to reduce, prevent, or otherwise ameliorate biofilm formation on at least a portion of a surface to which the bacteriophage is covalently tethered.

A medical device is provided whereby bioactive phage(s) is covalently attached to a surface of the device where a surface may be a coating such as a hydrogel coating material. Unlike prior attempts as using phage as agents for the prevention of biofilm that incorporate the phage into a matrix (e.g. U.S. Patent Application Publication No. US 2009/0191254), the present methods and devices use highly specific covalent attachment of the phage to the surface of the device (or surface of a coating) and are substantially to completely absent embedded phage within the surface or coating. Prior to the inventors' attempts to attach phage, direct covalent attachment required the presence of biological linkers such as antibodies, coat proteins or other indirect methods to maintain the bioactivity (infectivity) of the tethered phage. It was unknown whether possible conformational or structural changes resulting from direct tethering or tethering process would prevent phage binding to bacteria or effective transfer of phage material into the bacteria. The prevailing belief was that covalent attachment of phage would significantly affect the amount of active phage on the surface. Unexpectedly, the tethering of phage shows high infectivity, and allows for highly localized concentration of the phage to the surface of the device. As used herein, the term "tethering" is intended to mean a covalent attachment of phage to the surface of a device or a coating on a device. Tethering excludes incorporation or embedding of phage within a matrix such as a coating on the surface of a device.

Several medical devices, such as indwelling medical devices with phage tethered to a surface of the device are provided. In some embodiments, phages are tethered to a surface of a device intended to be contacted with a portion of a patient, such as the patient's skin. In some embodiments, phage are tethered to a surface of a device where biofilm formation is historically or may be formed such as on the surface of a device, for example, the surface of a catheter, including the luminal or extraluminal surfaces, or both. Medical devices including tethered phage are useful for introduction into the body of a subject. In some embodiments, a medical device includes one or more surfaces onto which a bacterial biofilm can form and an effective amount of tethered bacteriophage on one or more of these surfaces, wherein the bacteriophage composition inhibits formation of the bacterial biofilm on the surface of the medical device. As a non-limiting example, the medical device is suitable for surgical implantation within the body, such as an indwelling medical device. Such medical devices include, for example, a catheter (for example, a urinary catheter or an intravascular catheter), a stent, a shunt, an endotracheal tube, a gastric feeding tube, an artificial joint, an intrauterine device, an artificial voice prosthesis, a needleless connector for a central venous catheter, a tympanostomy tube, an artificial heart valve, a pacemaker, contact lens(es), nano- and microparticles such as those used for controlled delivery of therapeutics, among others known in the art. A medical device optionally is used to contact a body surface, but is not an indwelling medical device. For example, the medical device may be a contact lens, a suture, a bandage, a patch, or other surface contacting devices known in the art.

As used herein, a "subject" is a human, non-human primate, or other mammal. Illustrative examples of a subject include a human, bovine, equine, murine, rabbit, or guinea pig.

A bacteriophage useful for tethering includes any bacteriophage capable of infecting a bacterial host including those naturally or artificially produced illustratively from directed evolution approaches. Illustrative examples of bacteriophages include those capable of infecting bacteria of the family Enterobacteriaceae, illustratively, bacteria of the genus *Staphylococcus, Enterococcus, Pseudomonas, Proteus, Streptococcus*, or combinations thereof. Illustrative examples of phages include those capable of causing lysis or infection of *Staphylococcus aureus, Staphylococcus epidermidis*, coagulase-negative staphylococci, *Pseudomonas aeruginosa, Klebsiella pneumoniae, Escherichia coli, Enterobacter cloacae, Citrobacter koseri, Enterococcus faecalis, Enterococcus faecium, Providencia stuartii, Proteus mirabilis, Morganella morganii, Acinetobacter calcoaceticus, Enterobacter aerogenes, Streptococcus agalactiae, Streptococcus avium, Streptococcus Bovis, Streptococcus durans, Streptococcus faecalis, Streptococcus pneumoniae, Streptococcus pyogenes, Streptococcus suis, Streptococcus viridans, Streptococcus salivarius*, or other clinically relevant bacteria. Additional bacteriophage illustratively include those capable of infecting bacteria that cause Otitis Media or those that participate in joint infections, central line-associated bloodstream infections or other bacteria that are responsible for or play a role in biofilm formation on any surface.

In some embodiments, combinations of phages are used such as combinations of any phages listed herein, or others operable for preventing or treating biofilm formation or treating bacterial infection. A major advantage of this strategy is the ability to tether combinations of different bacteriophages to expand the specificity of the target bacteria.

In some embodiments, *Ps. aeruginosa, Pr. mirabilis* phages, or combinations thereof are used, illustratively those present in the phage library at the Centers for Disease Control and Prevention (CDC). Many of these phages produce plaques with the expanding halo that is characteristic of free polysaccharide depolymerase, an enzyme that can aid biofilm degradation [27-29]. One specific, non-limiting example includes bacteriophage 456. A staphylococcal bacteriophage composition optionally has $10^{10}$ PFU/ml of bacteriophage 456.

Illustrative examples of *Ps. aeruginosa* phages include F10, PA73, 119X, PA11, M6, F8, PA7, PA16, SD1-M, phiCTX, D3112, B3, phiKMV, PaP2, PaP3, D3, F116, and phiKZ. Characteristics of these phages can be found in Kwan, T., et al., *J. Bacteriol.*, 2006; 188:1184-1187.

Other phages tethered to a surface include phages are present in or isolated from raw sewage. Illustrative examples include, *Ps. aeruginosa* phages that such as those included in a cocktail published by Fu et al. (2010) [44] illustratively: ΦM4 (a typing phage from Colindale Laboratories), ΦE2005-24-39, ΦE2005-40-16, ΦW2005-24-39, Φ2005-37-18-03 (all isolated from raw sewage at a local wastewater treatment plant).

Phages include those that are obligately lytic (i.e. do not result in lysogeny). Illustrative examples of obligately lytic phages include ΦPaer4, ΦPaer14, and Φ109 (a typing phage from Colindale Laboratories) for *Pseudomonas aeruginosa*. Illustrative phages infecting *Proteus mirabilis* illustratively include ΦPmir1, ΦPmir32, ΦPmir34, ΦPmir37.

Illustrative phages infecting other uropathogens include those infecting KP1 (*Klebsiella pneumoniae*), PRE1 and PRE2 (*E. coli*), CK1 (*Citrobacter koseri*), EC1 and EC2 (*Enterobacter cloacae*).

It is well known to those of skill in the art that bacteriophages are present in the excretions of various animals, including livestock (for example, cattle and the like), pets (for example, dogs, cats, birds, and the like), poultry (for example, chickens and the like), and in sewage, and that bacteriophages can be isolated from these sources. Additionally, many of those skilled in the art maintain collections of bacteriophages with known specificities for certain species or strains of bacteria.

It is appreciated that any kind of bacteriophage can be employed, regardless of their source, as long as the bacteriophages have appropriate specificity for target bacteria, for example, *Staphylococcus* species, such as *Staphylococcus aureus*, and the coagulase-negative staphylococci (for example, *Staphylococcus epidermidis*), *Pseudomonas* species, such as *Pseudomonas aeruginosa*. In other words, there may be employed any bacteriophages that can achieve the objects of the present disclosure by infecting and, in certain embodiments, lysing, specific target host bacteria. Phages that produce depolymerase enzymes, which can effectively hydrolyze (degrade) the extracellular portion of the biofilm, are examples of phages used in the invention.

For example, members of the Myoviridae morphotype A1 family of bacteriophages (such as A, EW, K, Ph5, Ph9, Ph 10, Ph13, P1, P2, P3, P4, P8, P9, P 10, RG, $S_{B-1}$, (syn=Sb-1), S3K, Twort, φSK311, φ812, 06, 40, 58, 119, 130, 131, 200, and 1623), the Siphoviridae morphotype B2 family of bacteriophages (such as AC3, A8, A10, A13, b594n, D, HK2, N9, N15, P52, P87, S1, S6, $Z_4$, φpRE, 3A, 3B, 3C, 6, 7, 16, 21, 42B, 42C, 42E, 44, 47, 47A, 47C, 51, 54, 54×1, 70, 73, 75, 78, 81, 82, 88, 93, 94, 101, 105, 110, 115, 129/16, 174, 594n, 1363/14, 2460, and NN-*Staphylococcus*), and the Siphoviridae morphotype B1 family of bacteriophages (such as, AC1, AC2, A6"C", A9"C", $b^{581}$, CA-1, CA-2, CA-3, CA-4, CA-5, D11, L39×35, L54a, M42, N1, N2, N3, N4, N5, N7, N8, N10, N11, N12, N13, N14, N16, Ph6, Ph12, Ph14, UC-18, U4, U15, S1, S2, S3, S4, S5, X2, $Z_1$, φB5-2, φD, ω, 11, (syn=φ11), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80α, 82, 82A, 83A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, and 12100) infect *Staphylococcus* species (see, for example, The Bacteriophage Ecology Group web site).

Additionally, members of the Siphoviridae morphotype B1 family of bacteriophages (such as af, A7, B3, B33, B39, B1-1, C22, D3, D37, D40, D62, D3112, F7, F10, g, gd, ge, gf, Hw12, Jb19, KF1, L°, OXN-32P, 06N-52P, PCH-1, PC13-1, PC35-1, PH2, PH51, PH93, PH132, PMW, PM13, PM57, PM61, PM62, PM63, PM69, PM105, PM113, PM681, PM682, PO4, PP1, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-10, Pz, SD1, SL1, SL3, SL5, SM, φC5, φC11, φC11-1, φC13, φC15, φMO, φX, φ04, φ11, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, and NN-*Pseudomonas*), the Podoviridae morphotype C1 family of bacteriophages (such as A856, B26, C1-1, C1-2, C5, D, gh-1, F116, HF, H90, $K_5$, $K_6$, K104, K109, K166, K267, $N_4$, $N_5$, O6N-25P, PE69, Pf, PPN25, PPN35, PPN89, PPN91, PP2, PP3, PP4, PP6, PP7, PP8, PP56, PP87, PP114, PP206, PP207, PP306, PP651, Psp231a, Pssy401, Pssy9220, $ps_1$, PTB2, PTB20, PTB42, PX1, PX3, PX10, PX12, PX14, PYO70, PYO71, R, SH6, SH133, tf, $Ya_5$, $Ya_7$, φBS, ΦKf77, φ-MC, ΦmnF82, φPLS27, φPLS743, φS-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, and NN-*Pseudomonas*), and the Myoviridae morphotype A1 family of bacteriophages (such as AI-1, AI-2, B17, B89, CB3, Col 2, Col 11, Col 18, Col 21, C154, C163, C167, C2121, E79, F8, ga, gb, H22, $K_1$, M4, $N_2$, Nu, PB-1, (syn=PB 1), pf16, PMN17, PP1, PP8, Psa1, PsP1, PsP2, PsP3, PsP4, PsP5, PS3, PS17, PTB80, PX4, PX7, PYO1, PYO2, PYO5, PYO6, PYO9, PYO10, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, P1K, SLP1, SL2, $S_2$, UNL-1, wy, $Ya_1$, $Ya_4$, $Ya_{11}$, φBE, φCTX, φC17, φKZ, (syn=ΦKZ), φ-LT, Φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, and NN-*Pseudomonas*) infect *Pseudomonas* species, for example (see, for example, The Bacteriophage Ecology Group web site).

For example, members of the Podoviridae morphotype C3 family of bacteriophages (such as C2, C2F, E3, and E62), members of the PODOVIRIDAE, morphotype C1 family of bacteriophages (such as D1, SB24, 2BV, 182, and 225), members of the Myoviridae morphotype A1 family of bacteriophages (such as $DF_{78}$, F1, F2, 1, 2, 4, 14, 41, and 867), and members of the Siphoviridae morphotype B1 family of bacteriophages (such as DS96, H24, M35, P3, P9, SB101, S2, 2BII, 5; 182a, 705, 873, 881, 940, 1051, 1057, 21096C, and NN-*Enterococcus*) infect *enterococcus* species (see, for example, The Bacteriophage Ecology Group web site listing phages operable herein).

Screening of Bacteriophages to determine bacterial specificity, and the ability to selectively lyse pathogenic bacteria, can be carried out by a number of methods well known to those of skill in the art. (See, for example, U.S. Pat. No. 6,322,783.)

In some embodiments, phage isolates are free of toxin genes. Optionally, phages are obligately lytic, nontransducing, and effective at inhibiting growth and biofilm formation by pathogenic bacteria, and are unable to infect non-pathogenic and/or potentially beneficial microflora.

Bacteriophage-incorporating medical devices optionally inhibit biofilm formation for a prolonged period of time, such as at least twenty-four hours. In particular implementations, the bacteriophage incorporating medical devices inhibit biofilm formation for at least about a week, such as at least about thirty days, such as at least about a year.

Various embodiments are methods that are useful for inhibiting formation of a bacterial biofilm on a surface of a medical device such as an indwelling medical device. In some embodiments, the method includes contacting the surface of a medical device with an effective amount of a composition comprising one or more bacteriophages that inhibit formation of a bacterial biofilm prior to or following formation of the biofilm. In specific, non-limiting examples, the bacteriophage is a lytic bacteriophage. The bacteriophage optionally inhibits formation of biofilm by target bacteria, such as staphylococci that are capable of forming a staphylococcal bacterial biofilm. Exemplary bacterial biofilms prevented by the methods and devices of the invention include, but are not limited to those produced by or related to the presence of *S. aureus, S. epidermidis, Ps. aeruginosa, Pr. mirabilis, Escherichia coli, Klebsiella pneumoniae, Enterobacter* spp., *Enterococcus faecalis, Enterococcus faecium, Acinetobacter baumanii, Klebsiella oxytoca, Providencia* spp., *Morganella morganii*, coagulase-negative *Staphylococcus* spp., and *Citrobacter* spp. In some embodiments, the method includes tethering a phage composition to the surface of a medical device whereby the phages are bioactive and capable of inhibiting formation of a bacterial biofilm optionally prior to formation of the biofilm.

Bacteriophages are optionally attached or adhered to a surface of a medical device that is coated with a material, such as a gel (for example, a hydrogel) or polymeric (natural or synthetic) matrix, to which the bacteriophages are tethered. In some embodiments, the coating includes a surfactant, an antibacterial enzyme, an antibiotic, a growth or activity enhancing agent, or combinations thereof. Specific, non-limiting examples of the antibiotic include, for example, a beta-lactam, a cephalosporin, an aminoglycoside, a sulfonamide, a macrolide, a tetracycline, a silver salt, alloy or nanoformulation (such as nano-silver formulation(s)), elemental silver, antibiotics disclosed in U.S. Pat. No. 6,579, 539, combinations thereof, or others known in the art. A growth or activity enhancing agent includes divalent metal cations, such as $Ca^{2+}$ or $Mg^{2+}$.

In some embodiments, the medical device includes a surface having a coating, such as a viscous gel or material capable of forming a viscous gel, to which a bacteriophage composition may be tethered, such as a gel that includes free hydroxyl groups on the gel surface. In some embodiments, the medical device is coated with a hydrogel. Optionally, the medical device is pre-coated with the tetherable coating, while in other implementations, the embodiment includes coating the medical device with a viscous gel (such as a hydrogel), or material capable of forming a viscous gel.

In a specific disclosed example, the medical device is suitable for surgical implantation within the body of a subject, and is introduced into the body of a subject. Such medical devices illustratively include indwelling medical devices, for example, a catheter, a stent, a shunt, an endotracheal tube, a gastric feeding tube, an artificial joint, an artificial heart valve, an intrauterine device, an artificial voice prosthesis, a tympanostomy tube, a needleless connector for a central venous catheter, or a pacemaker. More specific examples include intravascular catheters (such as a central venous line) and intraurethral catheters (such as a bladder catheter), which are sometimes left in place for days or weeks.

A medical device optionally includes a lumen, which is often the site of bacterial biofilm occlusion and/or infection. The medical device is optionally a catheter and the bacteriophage composition is tethered within the lumen, to the external surfaces of the catheter, or both. A bacteriophage is optionally present in the lumen or on the external surfaces of the catheter prior to insertion of the catheter into a subject. Alternatively or in addition, a bacteriophage composition is present in the lumen or a portion of the catheter only after insertion of the catheter into a subject.

The medical device bearing tethered bacteriophage(s) is capable of preventing biofilm formation after being inserted into the body of a subject or associated with a surface body part of a subject (e.g. wound, burn, or other area in need) and coated with substances in the body of the subject. Illustratively, the substances that coat the medical device are platelets, plasma, or host proteins such as albumin, fibrinogen, fibronectin, and laminin.

Methods of forming a phage tethered medical device are provided. A surface of the medical device is optionally coated with a material coating, including one or more hydrogels, natural or synthetic polymer films, networks, matrices, sol-gels, silica-based coatings, and any material coating presenting pendant groups amenable to functionalization. One or more bacteriophages are tethered onto the outer surface of the viscous material. The bacteriophages are appreciated as not releasably tethered, such as by covalent interaction with active groups on the surface of the device or coating material.

Methods for introducing an indwelling medical device into the body of a subject that include surface tethered bacteriophage are provided. In some embodiments, a medical device coated with material that has surface tethered bacteriophage is provided. The medical device is then introduced into the body of the subject. In some embodiments, the coating is a polymeric film or matrix, such as a hydrogel. The medical device optionally remains in the body of the subject for a prolonged period of time, such as at least twenty-four hours, such as at least a week. In particular examples, the medical device remains in the body of the subject for at least thirty days, such as at least a year.

Surfaces of a medical device such as a surface prone to bacterial biofilm formation can be subjected to the methods of the present disclosure as a preventative measure prior to any biofilm formation to substantially avoid biofilm formation. Alternatively, at the first indication of biofilm formation, the methods may be used to prevent further biofilm formation and to remove the biofilm that has become deposited on a surface. Furthermore, in situations where there is a heavy build-up of biofilm on a surface, the methods may be used to reduce the level of biofilm or to remove it partially or completely.

Medical devices amenable to tethering to bacteriophage compositions have at least one active or activatable group exposed on the surface of the device or a coating thereon. Illustrative examples of active or activatable groups include hydroxyl, amine, carboxyl, nitrile, thioester, sulfhydryl, aldehyde, or other functional groups. Illustrative device surfaces include those composed of thermoplastic or polymeric materials such as polyethylene, polyethylene terephthalate (PET), polyamides, polyesters, polytetrafluoroethylene, polyurethane, latex, silicone elastomers, among others. Additionally, devices composed of natural materials, such as collagen and hyaluronic acid, could be modified. The surfaces of the device are optionally smooth or rough, for example, a smooth polymeric surface of a catheter lumen or a relatively rough PET patch for repairing an abdominal or vascular defect. Indwelling medical devices with metallic surfaces are also amenable to tethering to bacteriophage compositions. Such devices, for example bone and joint prosthesis, can be coated and tethered to a bacteriophage composition. During implant use, the bacteriophages remain bioactive and capable of lysing bacteria that may otherwise produce a significant biofilm. Particular indwelling medical devices illustratively include intravascular, peritoneal, pleural and urological catheters, heart valves, gastric feeding tubes, endotracheal tubes, tympanostomy tubes, intrauterine devices, artificial voice prostheses, prosthetic joints, stents, needleless connectors for central venous catheters, cardiac pacemakers, vascular shunts, and orthopedic, intraocular, or penile prosthesis.

Particular examples of medical devices to which phage are tethered include Bard hydrogel-coated silicone Foley type catheters (Lubri-Sil™), which are extensively used clinically. The Bard Lubri-Sil™ catheter has a covalently attached polyurethane matrix that is cross-linked with a poly(ethylene glycol) (PEG) hydrogel [50]. Phage are tethered to hydroxyl groups present on the surface of the PEG hydrogel.

Various methods can be employed to tether a surface of an indwelling medical device to a bacteriophage composition. For example, one of the simplest methods is to flush the surfaces of the medical device with a solution of the bacteriophage composition. Generally, treating the surfaces by a simple flushing technique would require convenient access to the medical device. For example, catheters are generally amenable to flushing with a solution containing the bacteriophage compositions disclosed herein. For use in flushing solutions, high titer (for example, $1\times10^{10}$ PFU/ml or higher) bacteriophage stocks are used. The flushing solution would normally be composed of sterile normal saline solutions. The bacteriophage composition may also be painted or sprayed on the medical device. In particular implementations, the medical device is dipped or immersed in the composition.

In some embodiments, tethering of bacteriophage is performed using NPC chemistry [48,49]. Illustratively, phage is tethered to a medical device surface using 4-nitrophenyl chloroformate (NPC) chemistry [51,52] to activate —OH groups in the surface of a PEG hydrogel and covalently link amines present on the proteinaceous phage surface to the PEG via urethane linkages. Other tethering chemistries are possible, including EDC/NHS and Michael-type additions.

In some embodiments, a medical device is pre-coated with a polymeric layer. Exemplary components of a polymeric layer include, but are not limited to, polylactic acid, polyglycolic acid and copolymers and mixtures thereof such as poly(L-lactide) (PLLA), poly(D,L-lactide) (PLA); polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-cotrimethylene carbonate) (PGA/PTMC), poly(D,L-lactide-co-caprolactone) (PLA/PCL), poly(glycolide-co-caprolactone) (PGA/PCL); polyethylene oxide (PEO), polydioxanone (PDS), polypropylene fumarate, poly (ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly (phosphazene), poly(phosphate ester), poly(amino acid) and poly(hydroxy butyrate), polydepsipeptides, maleic anhydride copolymers, polyphosphazenes, polyiminocarbonates, poly[(97.5% dimethyl-trimethylene carbonate)-co-(2.5% trimethylene carbonate)], cyanoacrylate, polyethylene oxide, hydroxypropylmethylcellulose, polysaccharides such as hyaluronic acid, chitosan and regenerate cellulose, and proteins such as gelatin and collagen, and mixtures and copolymers thereof, among others.

Furthermore, the bacteriophage compositions can be tethered to a surface of a medical device, simultaneously or alternately, with other agents, such as antibacterial agents, so as to more effectively inhibit bacterial biofilm formation, or, alternatively, prevent further biofilm formation or to remove the biofilm that has become deposited on a surface. For example, the bacteriophage compositions optionally includes a surfactant, an antibacterial enzyme, an antibiotic, a growth or activity enhancing agent, or combinations thereof.

Exemplary surfactants include biosurfactants (such as glycolipids, lipopeptides, depsipeptides, phospholipids, substituted fatty acids, lipopolysaccharides, surlactin, surfactin, visconsin, and rhamnolipids), sodium dodecyl sulfate, quaternary ammonium compounds, alkyl pyridinium iodides, Tween 80, Tween 85, Triton X-100, and the like. Exemplary antibacterial enzymes are a lytic enzyme, an acylase, an aminopeptidase, an amylase, a carbohydrase, a carboxypeptidase, a catalase, a cellulase, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a polysaccharide depolymerase, a proteolytic enzyme, a ribonuclease, a transglutaminase, a xylanase, and lysostaphin. Examples of antibiotics include antibiotics that interfere with or inhibit cell wall synthesis, such as penicillin, nafcillin, oxacillin, and other beta-lactam antibiotics; cephalosporins such as cephalothin; glycopeptides such as vancomycin; and other polypeptides. In particular examples, the growth or activity enhancing agent is a divalent metal cation, such as $Ca^{2+}$ or $Mg^{2+}$.

Coatings for the surface of medical devices illustratively include various hydrogel and polymeric coatings. One or more bacteriophages are optionally tethered to the hydrogel surface after the hydrogel is applied to the medical device. Illustrative examples of hydrogels include organic coatings formed by applying a mixture of an isocyanate, a polyol, polyvinylpyrrolidone, and a carrier to the surface of a medical device, as discussed in U.S. Pat. No. 5,160,790. Silane copolymers are optionally used to form suitably coated medical devices. For example, U.S. Pat. No. 6,908,681 discloses silane copolymers formed by reacting one or more polyisocyanates, a silane, and molecules having at least two functional groups that are reactive with isocyanate. U.S. Pat. No. 6,596,402 discusses medical device coatings formed by contacting the medical device with a copolymer including an organic group that reacts with water to form a silanol group. Suitable hydrogel coated catheters illustratively include Lubri-Sil™ catheters, available from C. R. Bard, Inc., of Covington, Ga.

In some embodiments, the hydrogel coating of the medical device includes an antimicrobial agent or another antibiotic, such as silver. Suitable catheters having a hydrogel coating that includes an antimicrobial agent illustratively include the Bardex catheters, available from C.R. Bard, Inc., that incorporate the Bacti-Guard silver antimicrobial agent. Optional coatings that include a fast-acting antimicrobial agent and a long-lasting antimicrobial agent are disclosed in U.S. Pat. No. 6,579,539.

Various aspects of the present invention are illustrated by the following non-limiting examples. The examples are for illustrative purposes and are not a limitation on any practice of the present invention. It will be understood that variations and modifications can be made without departing from the spirit and scope of the invention. Reagents illustrated herein are commercially available, and a person of ordinary skill in the art readily understands where such reagents may be obtained.

Example 1

Phage Production and Ability to Inhibit Planktonic Growth of Uropathogens

Phage are selected and propagated by standard techniques illustratively as described by [54], and in Carlson, K. 2005. *Working with bacteriophages: common techniques and methodological approaches*, p. 437-494 in E. Kutter and A. Sulakvelidze (ed.), Bacteriophages: Biology and Applications. CRC Press, New York. In one example, *S. epidermidis* 414 (HER 1292—Félix d'Hérelle Reference Center for Bacterial Viruses) are maintained at −80° C. Coagulase-negative *staphylococcus* phage 456 (Dean et al., *J. Hyg.* 71:261-270, 1973) (obtained from Health Protection Agency, Colindale, UK) is maintained as a lyophilized preparation stored at 4° C. The phage is propagated using the soft agar overlay technique (Adams, M., *Bacteriophages*, Interscience Publishers, London, 1959; Gratia, A., *Compt. Rend. Soc. Biol.* 122:812, 1936) and crude high titer phage broth cultures are prepared as described by Adams (Adams, M., *Bacteriophages*, Interscience Publishers, London, 1959) using *S. epidermidis* 414 as the host strain in Mueller-Hinton Broth (MHB), (Difco, Becton Dickinson, Sparks, Md.) containing 3 mM $MgCl_2$ and 4 mM $CaCl_2$ (added as $MgCl_2.6H_2O$ and $CaCl_2.2H_2O$). One ml of an 18 h culture of *S. epidermidis* 414 in MHB (cultured at 37° C.) is added to 49 ml of MHB containing 3 mM $MgCl_2$ and 4 mM $CaCl_2$. This is incubated at 37° C. with shaking at 250 revolutions per minute and the OD600 monitored until an absorbance of 0.3 is reached (Spectronic 21D Spectrophotometer, Spectronic Instruments Inc., Rochester, N.Y.). Phage 456 is added to a final concentration of $10^6$-$10^7$ plaque forming units/ml (PFU/ml). The culture is allowed to stand for 15 min at 37° C. and then incubated for 18 h at 37° C. with shaking at 100 rpm. Host cell debris is pelleted by centrifugation (4000×g for 20 min) and the supernatant containing phage filter sterilized (Millipore, Billerica, Mass.; 0.22 m pore size). The crude phage lysate is titered by plaque assay using the soft agar overlay technique on Mueller-Hinton agar (MHA) (Adams, M., *Bacteriophages*, Interscience Publishers, London, 1959; Gratia, A., *Compt. Rend. Soc. Biol.* 122:812, 1936), stored at 4° C., and used within a week. The phage are optionally purified by one or more techniques known in the art such as density gradient centrifugation (e.g. cesium chloride or sucrose), DEAE-cellulose chromatography, or chromatography using monolithic columns for HPLC [67] (i.e. anion or cation-exchange columns).

Figure 3:
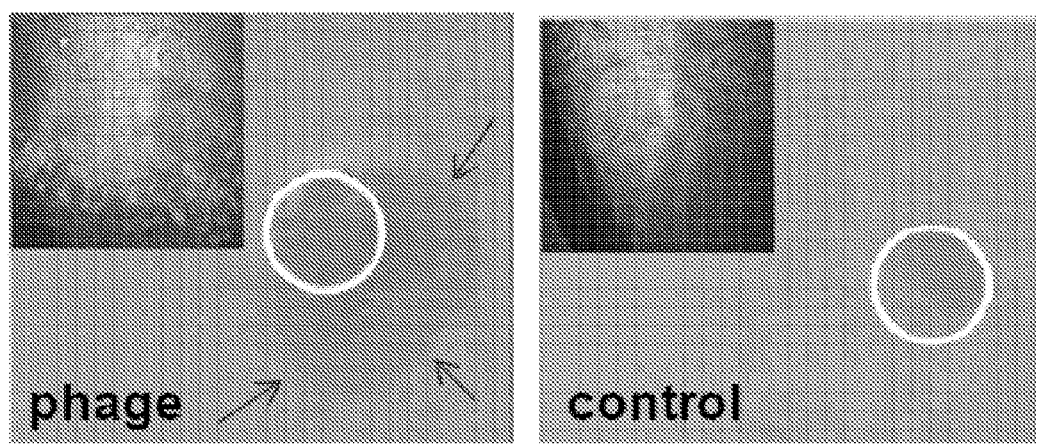
FIG. 3 illustrates that tethered phages retain infectivity and lytic ability wherein the images are transmitted light photographs of bacterial lawn exposed to catheter sample (white circle) and the arrows show area of bacterial lysis and wherein the inset illustrates confocal microscopy for tethered phage, wherein these figures illustrate that surface morphology is typical of the hydrogel-coated catheter.

Purified phage or combinations of phages are analyzed for their ability to inhibit planktonic growth of uropathogenics in a planktonic growth assay. Phages ΦPmir1, ΦPmir32, ΦPmir34, ΦPmir37, ΦPaer4, ΦPaer14, ΦM4 and Φ109 are prepared as above. A minimum inhibitory concentration assay is developed whereby individual wells of a 96-well plate are used to assay phage viability. Wells are inoculated $2\times10^6$ CFU of *Pr. mirabilis* or *Ps. aeruginosa* in 25% TSB. The bacteria are incubated at 37° C. for 2 hours. A titration of individual phage are added individually to wells of the plate in a titration from 0 (control) or phage amounts from $1\times10^3$ to $1\times10^9$ PFU/ml and incubated with the bacteria for 6 hours at 37° C. Following incubation, the amount of viable bacterial are determined by absorbance (600 nm) to access bacterial growth in the presence of phage. FIG. 2 illustrates the ability of different phage strains to inhibit growth of *Pr. mirabilis*. FIG. 3 illustrates the ability of different phage strains to inhibit growth of *Ps. aeruginosa*. The results indicate that individual phages are able to inhibit growth of more than one bacterial strain of a given species. Also, a mixture of a few phages is able to prevent planktonic growth of all but multiple *Ps. aeruginosa* and *Pr. mirabilis* host strains. Minimum initial phage concentrations required for control are as low as $5\times10^3$ PFU/mL (highest tested was $5\times10^8$ PFU/mL, and data suggest that the more difficult-to-control bacterial strains could be achieved with $1\times10^{10}$ PFU/ml).

Example 2

Tethering Phage to a Surface of a Catheter

Lubri-Sil™ all-silicone French Foley catheters are used (C. R. Bard, Covington, Ga.). Optionally, Lubri-Cath™ latex catheters or Lubri-Sil I.C.™ silicone catheters with silver (C. R. Bard, Covington, Ga.) are used. Lubri-Sil™ catheters are formed from hydrogel-coated silicone, Lubri-Cath™ catheters are formed from hydrogel-coated latex, and Lubri-Sil I.C.™ catheters are formed from hydrogel-coated silicone with silver alloy. Each catheter has a surface attached polyurethane matrix that is cross-linked with a poly(ethylene glycol) (PEG) hydrogel [50]. Hydrogel coatings on catheters are activated with 4-nitrophenyl chloroformate (NPC) (23 mM in THF or acetone) such as described in [48,53]. NPC activation of the hydrogel does not, in itself, affect bacterial adhesion. Residual NPC is removed by rinsing in THF or acetone. Residual THF or acetone is removed by rinsing in purified water. The activated surface is then incubated with bacteriophage diluted to $1\times10^7$ PFU ml$^{-1}$ or higher in PBS for at least 30 min to allow phage tethering via primary amines. Residual activated NPC sites without bound phage are quenched in 20 mM glycine to block further reactive groups. Non-tethered phages are removed through additional washing steps, including but not limited to sonication and rinsing in any of wash solutions including buffers such as PBS or PBS with at least 0.9 M NaCl, AUM, or at least 1% solutions of anionic, cationic, zwitterionic, or nonionic detergents such as Tween-20, Triton X-100, N-lauroylsarcosine, 3-[(3-cholamidopropyl)dimethylammonio]-1-propanesulfonate, sodium deoxycholate, cetyltrimethylammonium bromide, octyl-β-glucoside. Following phage tethering, rinsing recovers fewer free, residual phages from catheters with tethered phages than from those with passively adsorbed phages, indicating covalent attachment of phages via the tethering reaction. The density of tethered phages is readily controlled by modifying the concentration of phage suspension. Other methods of binding protein to PEG hydrogels are found in D'Urso and Fortier, *Biotech. Tech.*, 1994, 8:71-76.

The tethering is repeated using purified *Ps. aeruginosa* phage labeled with AlexaFluor 555 dye and tethered onto Lubri-Sil™ urinary catheter segments using NPC chemistry as described above. The density of tethered phages as a function of coating concentration is determined using quantitative microscopy essentially as described [55].

FIG. 3 (left panel inset) demonstrates by confocal microscopy that significant and specific tethering of phage to activated hydrogels is obtained and that tethered phages retain bioactivity.

Example 3

Tethered Phage are Highly Lytic

Figure 4:
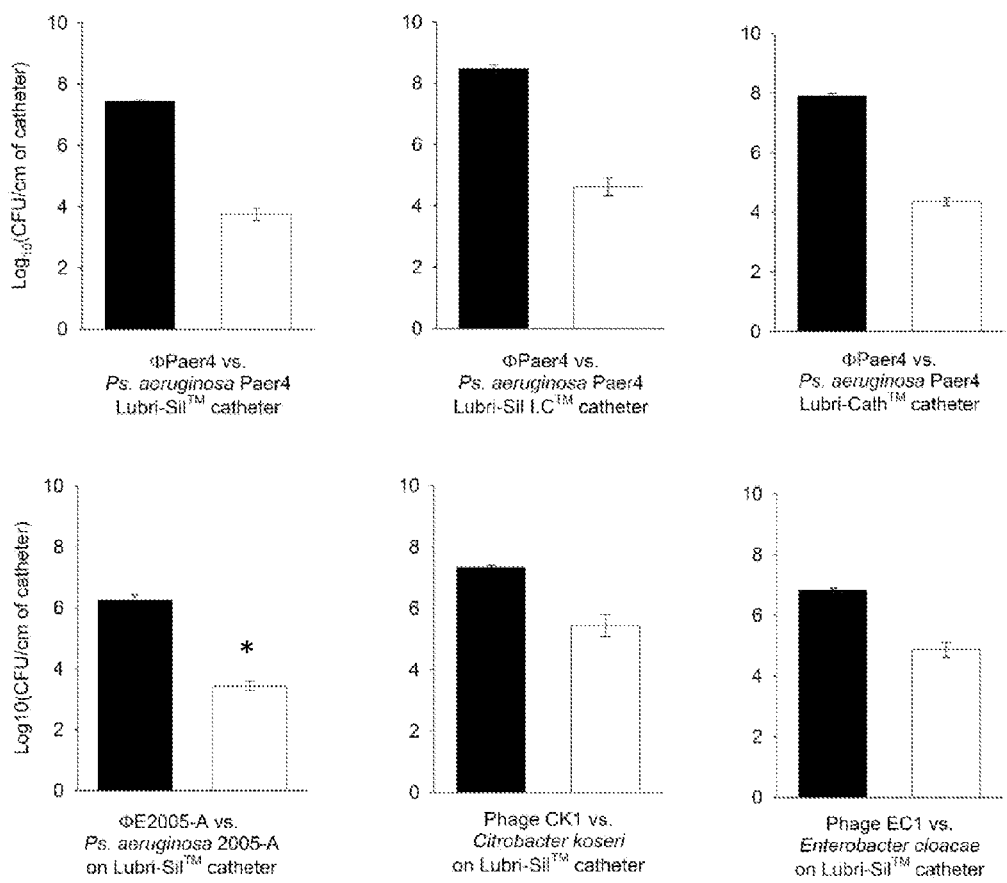
FIG. 4 illustrates the ability of catheter tethered phages to inhibit growth of *Ps. aeruginosa, Enterobacter cloacae*, and *Citrobacter koseri* on catheters including tethered phages where black bars indicate phage-free catheter segments; white bars indicate catheters with tethered phages, and wherein data are mean CFU/cm±standard error; and all white bars illustrate statistically significant differences (all P<0.05) and all data are from 16 Fr. Foley catheters.

The phage tethered hydrogel coated catheters of Example 2 are cut into 1 cm$^2$ segments. Control groups include (i) unmodified catheter, (ii) unactivated catheters (no NPC treatment) exposed to bacteriophage solution, and (iii) activated catheters coated with heat-inactivated phage. The presence of viable, tethered phages is determined by placing phage-treated and control catheter segments on a lawn of bacteria. As shown in FIG. 3A, specifically tethered *Ps. aeruginosa* or *Pr. mirabilis* phage retain infectivity and lytic activity as demonstrated by the presence of the telltale halo indicating bacterial lysis. Similarly treated catheter segments are placed into 3 ml AUM containing approximately $3\times10^5$ CFU/ml bacteria and incubated in shaking culture at 37° C. for 12 h. As shown in FIG. 4, significantly less biofilm develops on catheter segments presenting tethered phage than on unmodified Lubri-Sil™ (hydrogel-coated silicone), Lubri-Cath™ (hydrogel-coated latex), and Lubri-Sil I.C.™ (hydrogel-coated silicone with silver alloy) catheters.

In additional experiments, a conditioning film is simulated on the catheter lumen to assess its affect on biofilm formation and phage effectiveness. Filter-sterilized whole human serum (complement inactivated at 56° C. for 30 min) is instilled into both phage-tethered and untreated control catheter segment lumens in a Drip Flow Reactor (mDFR) (Biosurface Technologies) [43,44] and incubated for 2 h at 37° C. The presence of the serum conditioning film is confirmed by fluorescent microscopy. Catheter segments incubated with serum are cut in segments as above. The segments are washed with sterile PBS three times (1 min per wash), incubated with 3% bovine serum albumin at 37° C. for 1 h to prevent non-specific binding, and rewashed three times in PBS. The segments are then incubated with goat anti-human IgG (H+L) fluorescein isothiocyanate (FITC) conjugate (Zymed Laboratories, San Francisco, Calif.) for 1 h at room temperature, and washed three times in sterile PBS. Catheter segments not coated with serum are used as controls. All catheter segments are examined using a Zeiss Axioplan 2 Imaging Fluorescent Microscope (10×, 20× and 100× objective lenses), (Carl Zeiss Light Microscopy, Göttingen, Germany) with a FITC filter (filter set #41001, excitation filter, 480/40×; emission filter, 535/50 m; dichroic mirror, 505 nm; Chroma Technology Corp., Rockingham, Vt.). Samples are photographed using a Zeiss Axiocam high resolution digital camera (Carl Zeiss Light Microscopy, Göttingen, Germany). Images are analyzed using Axiovision 4.0 software (Carl Zeiss Vision, München Hallbergmoos, Germany). Both test catheter segments and control segments are photographed using the same exposure time.

The tethered phages remain bioactive and reduce biofilm formation relative to controls.

Example 4

Tethered Phage Coated Catheter Systems Demonstrate Superior Prevention of Biofilm Development Relative to Adsorbed Phage Devices The phage tethered hydrogel coated catheters of Example 2 are compared to catheters including coatings with adsorbed phage contained within the coating material of U.S. Patent Publication No. US 2009/0191254 A1 and corresponding International Publication No. WO/2006/063176. Comparisons are made using the methods of Example 3.

Figure 5:
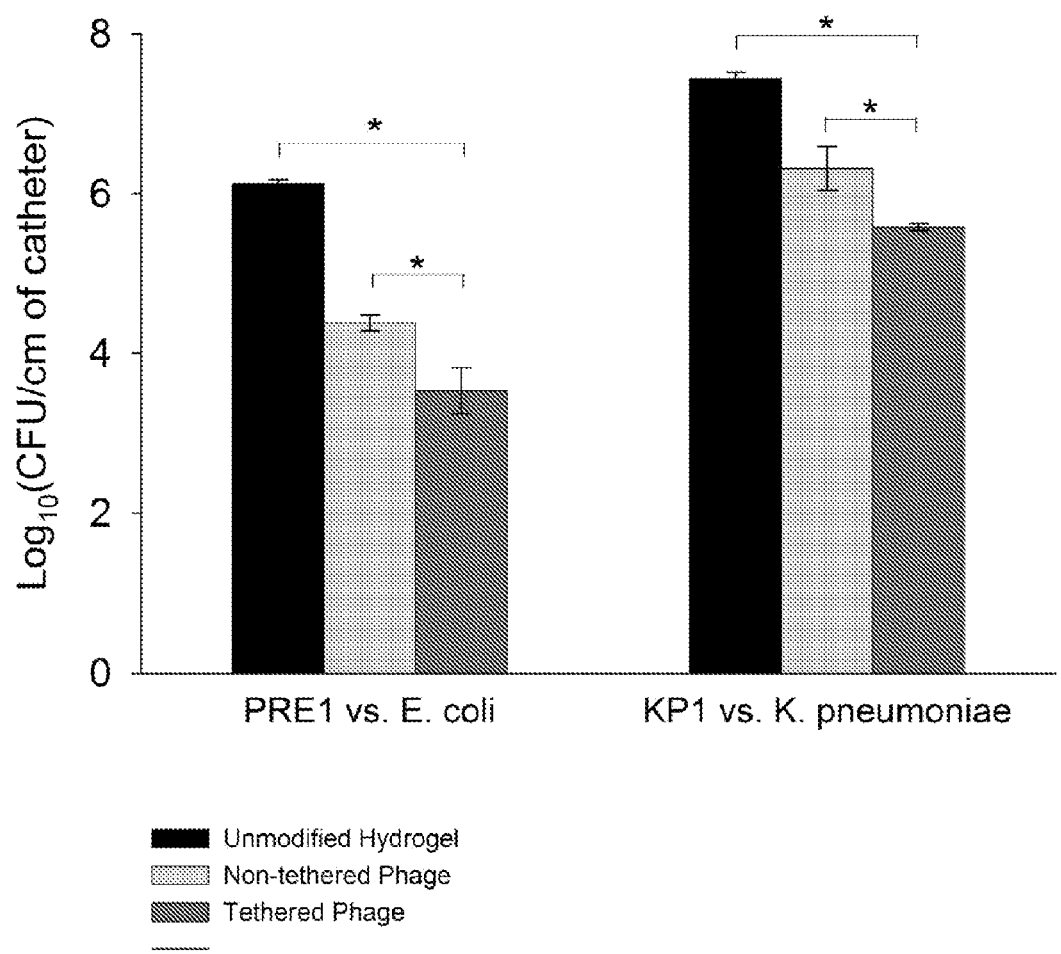
FIG. 5 illustrates superior efficacy of tethered phages relative to unmodified hydrogel coated catheter surfaces and hydrogel coated catheter surfaces with phages passively adsorbed therein.

As is illustrated in FIG. 5, in batch culture experiments, tethered *K. pneumoniae* phage KP1 and tethered *E. coli* phage PRE1 each reduce biofilm development on 16 Fr. Lubri-Sil™ catheter pieces more than passively adsorbed phages of catheters prepared as in US 2009/0191254 A1. Data are mean CFU/cm±standard error. Significant differences are indicated by asterisks ($P<0.05$, Tukey Multiple Comparison test). These data demonstrate that the tethered phage can effect significantly more biofilm inhibition than non-tethered, passively adsorbed phage of US 2009/0191254.

Example 5

Tethered Phages Prevent Biofilm Formation in a Urinary Catheter Model System

*Ps. aeruginosa* or *Pr. mirabilis* phage are tethered to Bard Lubri-Sil™ Foley catheters at the catheter luminal surface that includes a PEG hydrogel essentially as described in Example 2 using a titer of, for example, $1.0\times10^8$ to $5\times10^{10}$ PFU ml$^{-1}$. Control groups include (i) unmodified catheters, (ii) unactivated catheters (no NPC treatment) exposed to bacteriophage solution, and (iii) catheters coated with inactivated phages. The ability of specifically tethered phages to induce infectivity and bacterial cell lysis are examined under dynamic conditions.

Biofilms are grown on catheters in a modified Drip Flow Reactor (mDFR) (Biosurface Technologies) [43,44] or similar catheter immobilizing device. The device is composed of four separate chambers, each with a sealing lid. The original device is modified to allow the connection of catheter segments of any lumen size to influent and effluent ports within the device. Before each experiment, the device containing the catheters is sterilized using ethylene oxide gas. The mDFR is coupled to a batch culture of *Ps. aeruginosa* or *Pr. mirabilis* phage in Artificial Urine Medium (AUM) and a sterile medium reservoir containing half-strength AUM. The culture is pumped through the mDFR for 2 h (1 ml/min), irrigating the catheter segments attached inside for initial bacterial adhesion. The mean CFU per ml of the batch culture is approximately $10^3$ during this during this 2-h period. This is followed by irrigation for 22-94 h with sterile AUM (0.5 ml/min) to establish a biofilm. Catheters are collected after several of 2, 6, 24, 48, 72, and 96 hours after bacterial inoculation. Optionally, bacterial exposure is preceded by prolonged exposure (e.g. 15 h) to sterile AUM (1 ml/min). All mDFR experiments are carried out at 35° C. in triplicate.

Following exposure to biofilm forming organisms, the catheter is cut into smaller sections, each with an internal curved surface area of approximately 1 cm$^2$. For example, a catheter of 16 Fr size produces an internal surface area of 0.94 cm$^2$. Three of these sections are sliced vertically into two halves, and each halved section washed gently in 5 ml phosphate-buffered saline (PBS) (7.2 pH) to remove planktonic and loosely adherent cells. Individual sections are subjected to high-speed vortexing in 5 ml PBS for 15 s, followed by sonication for 10 min at 42 kHz (Branson 2510; Branson, Danbury, Conn.), further vortexing for 15 s, sonication for 5 min, and a final vortexing for 15 s. Earlier studies indicated that the process removed essentially all of the viable cells from the surface of the catheter and that sonication is not associated with loss of viability of the cells in suspension (data not shown). In each experiment, the viable bacterial counts for the three 1-cm$^2$ sections of catheter are established and the mean viable count, expressed as CFU/cm$^2$, is determined.

Phages in the luminal fluid of catheter samples are quantified prior to catheter processing using the soft agar overlay method [54]. Detection of lytic phage in the luminal fluid indicates phage infection and replication in biofilm cells. When bacterial adhesion is preceded by 15 h of sterile AUM flow and catheters are tested after this washout period but before bacterial adhesion, fewer free viable phages are recovered from the luminal fluid of catheters with tethered phages vs. non-tethered passively adsorbed phages, indicating that covalent tethering to NPC-modified hydrogels is occurring; phage titers in luminal fluid collected at later time points show that this does not adversely affect later replication of the tethered phages. Biofilm development is assessed by viable counts and fluorescence microscopy. For viable count data, catheter segments are processed using standardized protocols to recover biofilm organisms, and organisms from the biofilms are quantified by the plate count procedure [43,44] using TSA, or using *Pseudomonas* Isolation Agar (BD Bioscience) and C1 agar [56], which are selective for *Ps. aeruginosa* and *Pr. mirabilis*, respectively. Counts are expressed as colony forming units per cm$^2$ of catheter lumen surface. All experiments are performed a minimum of three times. Bacterial and phage counts are $log_{10}$-transformed, and differences in microbial recovery are analyzed using ANOVA. The results indicate that phage tethered to surfaces are active and can reduce biofilm development in the catheter lumen by 2 to 5 orders of magnitude over the first 24 h.

For microscopy analyses, additional catheter segments are retained prior to processing for viable count. Biofilm organisms are fixed and stained with DAPI or processed immediately with BacLight™ LIVE/DEAD stain, and examined using a confocal microscope. Parameters such as surface coverage and total biomass are analyzed using the COMSTAT program [57], round segments of each sampled catheter are punched out and affixed to glass slides for microscopic examination. The experiments demonstrate that the presence of tethered phage reduces the amount of biofilm organisms adhered to the surface of the catheter.

Example 6

Tethered Phage Prevents Biofilm Formation on Urinary Catheters In Vivo

A rabbit subcutaneous model of device-related infection is used to determine the effectiveness of phage-tethered catheters is performed essentially as described [58,59,60,61]. The phage-tethered catheters of Example 2 are pre-incubated with bacteria ($10^5$ CFU, incubation for 2 hours) as in Example 4 prior to implantation because previous work demonstrated that this approach resulted in established biofilms compared to biomaterials co-implanted with bacteria [58,59,62]. A general experimental design is illustrated in Table 1:

| group | bacteria | day 2 | day 7 | day 14 |
|---|---|---|---|---|
| catheter | Ps. aeruginosa | 6 | 6 | 6 |
| catheter exposed to phage (no tethering) | Ps. aeruginosa | 6 | 6 | 6 |
| catheter + phage | Ps. aeruginosa | 6 | 6 | 6 |
| catheter | Pr. mirabilis | 6 | 6 | 6 |
| catheter exposed to phage (no tethering) | Pr. mirabilis | 6 | 6 | 6 |
| catheter + phage | Pr. mirabilis | 6 | 6 | 6 |

The phage-tethered catheters are implanted in subcutaneous pockets created by blunt dissection in the backs of New Zealand White rabbits (2 kg). Each rabbit receives 2 implants for each experimental group for a given bacteria (6 implants/animal). No systemic antibiotics are administered. Rabbits are euthanized at 3, 7, and 14 days post-implantation. These time points are selected based on published results with this model of device-related infection [58, 59] and provide different time points to examine the evolution of the biofilm. Biofilm colonization and growth are evaluated using the standard methods described above. Each catheter sample is divided into segments for: (1) microscopic/immunohistochemical analyses of biofilm and host inflammatory responses (leukocyte recruitment) and scanning electron microscopy; and (2) analyses of viable bacterial counts by recovering and quantifying biofilm by the plate count procedure. Finally, colonies cultured from surface-attached biofilms (if any) are identified using the Vitek II bacterial identification system to verify that any bacteria remaining on implants at retrieval are the same as those used in the initial contamination.

Based on the in vitro studies of Examples 2-5, phages covalently tethered onto hydrogel coatings on urinary catheter segments are expected to significantly reduce biofilm formation compared to controls in this animal model of device-related infection.

Example 7

Phage Tethering to Monolayers of Alkanethiols Remain Bioactive

Figure 6:
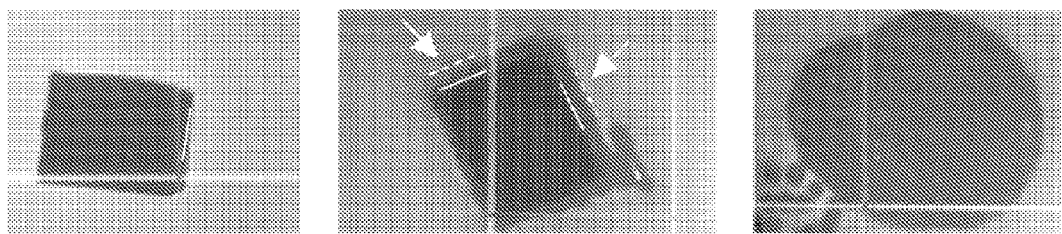
FIG. 6 illustrates that tethered phages retain infectivity and lytic ability wherein biomaterial is outlined with solid white lines, and outer edge of lysed bacterial zone is indicated with hashed white lines and wherein no evidence of phage-mediated lysis is associated with the biomaterial that was not exposed to phage (left) and wherein the 'halo' (arrows) surrounding the biomaterial with tethered phage (center) shows bacterial lysis due to phage action that occurs when phage is applied directly to the bacterial lawn (right).

Self-assembled monolayers of alkanethiols presenting non-fouling PEG and COOH anchoring groups are used as a model biomaterial. Petrie T A, Capadona J R, Reyes C D, Garcia A J, *Biomaterials,* 2006; 27(31):5459-70. This system provides a robust and simple system to quantify ligand tethered densities and activities. In this experiment, the COOH anchoring groups are activated with NHS/EDC and incubated with a partially purified suspension of one highly concentrated *P. aeruginosa* phage to allow phage tethering via primary amines. Residual active sites are quenched with glycine, and the samples are sonicated briefly and repeatedly rinsed in PBS to remove loosely associated phages. The biomaterials are placed active-side-down on a soft agar layer seeded with *P. aeruginosa,* and incubated overnight at 37° C. Biomaterials that have tethered phage display the 'halo' characteristic of bacterial lysis, whereas the control sample with no tethered phage showed no evidence of lysis (FIG. 6). These results demonstrate that tethered phages retain their ability to infect and lyse host bacteria.

REFERENCE LIST

1. Services USDoHaH. Action Plan to Prevent Healthcare-Associated Infections. 2009; http://www.hhs.gov/ash/initiatives/hai/actionplan/index.html.
2. Bryers J D. Medical biofilms. Biotechnol Bioeng. 2008; 100(1):1-18.
3. Klevens R M, Edwards J R, Richards C L, Jr., Horan T C, Gaynes R P, Pollock D A, et al. Estimating health care-associated infections and deaths in U.S. hospitals, 2002. Public Health Rep. 2007; 122(2):160-6.
4. Weinstein M P, Towns M L, Quartey S M, Mirrett S, Reimer L G, Parmigiani G, et al. The clinical significance of positive blood cultures in the 1990s: a prospective comprehensive evaluation of the microbiology, epidemiology, and outcome of bacteremia and fungemia in adults. Clin Infect Dis. 1997; 24(4):584-602.
5. Saint S. Clinical and economic consequences of nosocomial catheter-related bacteriuria. Am J Infect Control. 2000; 28(1):68-75.
6. Platt R, Polk B F, Murdock B, Rosner B. Mortality associated with nosocomial urinary-tract infection. N Engl J Med. 1982; 307(11):637-42.
7. Givens C D, Wenzel R P. Catheter-associated urinary tract infections in surgical patients: a controlled study on the excess morbidity and costs. J Urol. 1980; 124(5):646-8.
8. Tambyah P A, Knasinski V, Maki D G. The direct costs of nosocomial catheter-associated urinary tract infection in the era of managed care. Infect Control Hosp Epidemiol. 2002; 23(1):27-31.
9. Siebert J D, Thomson R B, Jr., Tan J S, Gerson L W. Emergence of antimicrobial resistance in gram-negative bacilli causing bacteremia during therapy. Am J Clin Pathol. 1993; 100(1):47-51.
10. Maki D G, Tambyah P A. Engineering out the risk for infection with urinary catheters. Emerg Infect Dis. 2001; 7(2):342-7.
11. Daifuku R, Stamm W E. Association of rectal and urethral colonization with urinary tract infection in patients with indwelling catheters. JAMA 1984; 252(15): 2028-30.
12. Rogers J, Norkett D I, Bracegirdle P, Dowsett A B, Walker J T, Brooks T, et al. Examination of biofilm formation and risk of infection associated with the use of urinary catheters with leg bags. J Hosp Infect. 1996; 32(2):105-15.
13. Tambyah P A, Halvorson K T, Maki D G. A prospective study of pathogenesis of catheter-associated urinary tract infections. Mayo Clinic Proc. 1999; 74(2):131-6.
14. Stickler D J. Bacterial biofilms and the encrustation of urethral catheters. Biofouling. 1996; 9(4):293-305.
15. Ganderton L, Chawla J, Winters C, Wimpenny J, Stickler D. Scanning electron microscopy of bacterial biofilms on indwelling bladder catheters. Eur J Clin Microbiol Infect Dis. 1992; 11(9):789-96.
16. Stickler D, Ganderton L, King J, Nettleton J, Winters C. *Proteus mirabilis* biofilms and the encrustation of urethral catheters. Urol Res. 1993; 21(6):407-11.
17. Olson M E, Nickel J C, Khoury A E, Morck D W, Cleeland R, Costerton J W. Amdinocillin treatment of catheter-associated bacteriuria in rabbits. J Infect Dis. 1989; 159(6):1065-72.
18. Johnson J R, Kuskowski M A, Wilt T J. Systematic review: antimicrobial urinary catheters to prevent catheter associated urinary tract infection in hospitalized patients. Ann Intern Med. 2006; 144(2):116-26.

19. Schumm K, Lam T B. Types of urethral catheters for management of short-term voiding problems in hospitalised adults. Cochrane Database Systematic Rev. 2008; 2:004013.

20. Lai K K, Fontecchio S A. Use of silver-hydrogel urinary catheters on the incidence of catheter-associated urinary tract infections in hospitalized patients. Am J Infect Control. 2002; 30(4):221-5.

21. Morris N S, Stickler D J, Winters C. Which indwelling urethral catheters resist encrustation by *Proteus mirabilis* biofilms? Br J Urol. 1997; 80(1):58-63.

22. Pugach J L, DiTizio V, Mittelman M W, Bruce A W, DiCosmo F, Khoury A E. Antibiotic hydrogel coated Foley catheters for prevention of urinary tract infection in a rabbit model. J Urol. 1999; 162:883-7.

23. Donlan R M. Preventing biofilms of clinically relevant organisms using bacteriophage. Trends Microbiol. 2009; 17(2):66-72.

24. Geier M R, Trigg M E, Merril C R. Fate of bacteriophage lambda in non-immune germ-free mice. Nature. 1973; 246(5430):221-3.

25. Smith H W, Huggins M B. Successful treatment of experimental *Escherichia coli* infections in mice using phage: its general superiority over antibiotics. J Gen Microbiol. 1982; 128(2):307-18.

26. Bruttin A, Brussow H. Human volunteers receiving *Escherichia coli* phage T4 orally: a safety test of phage therapy. Antimicrob Agents Chemother. 2005; 49(7): 2874-8.

27. Hanlon G W, Denyer S P, Olliff C J, Ibrahim L J. Reduction in exopolysaccharide viscosity as an aid to bacteriophage penetration through *Pseudomonas aeruginosa* biofilms. Appl Environ Microbiol. 2001; 67(6): 2746-53.

28. Hughes K A, Sutherland I W, Clark J, Jones M V. Bacteriophage and associated polysaccharide depolymerases; novel tools for study of bacterial biofilms. J Appl Microbiol. 1998; 85(3):583-90.

29. Lu T K, Collins J J. Engineered bacteriophage targeting gene networks as adjuvants for antibiotic therapy. Proc Natl Acad Sci USA. 2009; 106(12):4629-34.

30. Doolittle M M, Cooney J J, Caldwell D E. Tracing the interaction of bacteriophage with bacterial biofilms using fluorescent and chromogenic probes. J Industrial Microbiol. 1996; 16(6):331-41.

31. Biswas B, Adhya S, Washart P, Paul B, Trostel A N, Powell B, et al. Bacteriophage therapy rescues mice bacteremic from a clinical isolate of vancomycin-resistant *Enterococcus faecium*. Infect Immunity. 2002; 70(1):204-10.

32. Chanishvili N, Chanishvili T, Tediashvili M, Barrow P A. Phages and their application against drug-resistant bacteria. J Chem Tech Biotech. 2001; 76(7):689-99.

33. Carlton R M, Noordman W H, Biswas B, de Meester E D, Loessner M J. Bacteriophage P100 for control of *Listeria monocytogenes* in foods: Genome sequence, bioinformatic analyses, oral toxicity study, and application. Regul Toxicol Pharmacol. 2005; 43(3):301-12.

34. Jones J B, Jackson L E, Balogh B, Obradovic A, Iriarte F B, Momol M T. Bacteriophages for plant disease control. Ann Rev Phytopathol. 2007; 45:245-62.

35. Lehman S M. Development of a bacteriophage-based biopesticide for fire blight. [PhD Thesis]. St. Catharines, ON: Brock University; 2007.

36. Weber-Dabrowska B, Mulczyk M, Gorski A. Bacteriophage therapy of bacterial infections: an update of our institute's experience. Arch Immunol Ther Exp (Warsz). 2000; 48(6):547-51.

37. Gorski A, Miedzybrodzki R, Borysowski J, Weber-Dabrowska B, Lobocka M, Fortuna W, et al. Bacteriophage therapy for the treatment of infections. Curr Opin Investig Drugs. 2009; 10(8):766-74.

38. Markoishvili K, Tsitlanadze G, Katsarava R, Morris J G J, Sulakvelidze A. A novel sustained-release matrix based on biodegradable poly(ester amide)s and impregnated with bacteriophages and an antibiotic shows promise in management of infected venous stasis ulcers and other poorly healing wounds. Int J Dermatol. 2002; 41(7):453-8.

39. Wright A, Hawkins C H, Anggard E E, Harper D R. A controlled clinical trial of a therapeutic bacteriophage preparation in chronic otitis due to antibiotic-resistant *Pseudomonas aeruginosa*; a preliminary report of efficacy. Clin Otolaryngol. 2009; 34(4):349-57.

40. Mermel L A. Prevention of intravascular catheter-related infections. Ann Intern Med. 2000; 132(5):391-402.

41. Maki D G, Kluger D M, Crnich C J. The risk of bloodstream infection in adults with different intravascular devices: a systematic review of 200 published prospective studies. Mayo Clin Proc. 2006; 81(9):1159-71.

42. Bauer T W, Schils J. The pathology of total joint arthroplasty II. Mechanisms of implant failure. Skeletal Radiol. 1999; 28(9):483-97.

43. Curtin J J, Donlan R M. Using bacteriophages to reduce formation of catheter-associated biofilms by *Staphylococcus epidermidis*. Antimicrob Agents Chemother. 2006; 50(4):1268-75.

44. Fu W, Forster T, Mayer O, Curtin J J, Lehman S M, Donlan R M. Bacteriophage cocktail for the prevention of biofilm formation by *Pseudomonas aeruginosa* on catheters in an in vitro model system. Antimicrob Agents Chemother. 2010; 54(1):397-404.

45. Kreger B E, Craven D E, Carling P C, McCabe W R. Gram-negative bacteremia. III. Reassessment of etiology, epidemiology and ecology in 612 patients. Am J Med. 1980; 68:332-43.

46. Kuikka A, Valtonen V V. Factors associated with improved outcome of *Pseudomonas aeruginosa* bacteremia in a Finnish university hospital. Eur J Clin Microbiol Infect Dis. 1998; 17(10):701-8.

47. Thiel K. Old dogma, new tricks-21st Century phage therapy. Nat Biotechnol. 2004; 22(1):31-6.

48. Petrie T A, Raynor J E, Reyes C D, Burns K L, Collard D M, Garcia A J. The effect of integrin-specific bioactive coatings on tissue healing and implant osseointegration. Biomaterials. 2008; 29(19):2849-57.

49. Petrie T A, Raynor J E, Dumbauld D W, Lee T T, Jagtap S, Templeman K L, et al. Multivalent integrin-specific ligands enhance tissue healing and biomaterial integration. Sci Transl Med. 2010; 2(45):45ra60.

50. Elton R K, inventor; C.R. Bard, Inc., assignee. Flexible lubricious organic coatings. U.S. Pat. No. 5,179,174. 1993.

51. Miron T, Wilchek M. Immobilization of proteins and ligands using chlorocarbonates. Methods Enzymol. 1987; 135:84-90.

52. Li J T, Carlsson J, Lin J N, Caldwell K D. Chemical modification of surface active poly(ethylene oxide)-poly (propylene oxide) triblock copolymers. Bioconjug Chem. 1996; 7(5):592-9.

53. Raynor J E, Petrie T A, Garcia A J, Collard D M. Controlling cell adhesion to titanium: Functionalization of poly[oligo(ethylene glycol methacrylate] brushes with cell-adhesive peptides. Adv Mater. 2007; 19:1724-8.
54. Adams M N. Bacteriophages. New York: Interscience Publishers; 1959.
55. Petrie T A, Stanley B T, Garcia A J. Micropatterned surfaces with controlled ligand tethering. J Biomed Mater Res A. 2009; 90(3):755-65.
56. Clayton C L, Chawla J C, Stickler D J. Some observations on urinary tract infections in patients undergoing long-term bladder catheterization. J Hosp Infect. 1982; 3(1):39-47.
57. Williams M M, Yakrus M A, Arduino M J, Cooksey R C, Crane C B, Banerjee S N, et al. Structural analysis of biofilm formation by rapidly and slowly growing nontuberculous mycobacteria. Appl Environ Microbiol. 2009; 75(7):2091-8.
58. Darouiche R O, Mansouri M D, Meade R. In-vitro and in-vivo activity of antimicrobial-coated prosthetic heart valve sewing cuffs. J Heart Valve Dis. 2002; 11(1):99-104.
59. Darouiche R O, Mansouri M D, Gawande P V, Madhyastha S. Efficacy of combination of chlorhexidine and protamine sulphate against device-associated pathogens. J Antimicrob Chemother. 2008; 61(3):651-7.
60. Morck D W, Olson M E, McKay S G, Lam K, Prosser B, Cleeland R, et al. Therapeutic efficacy of fleroxacin for eliminating catheter-associated urinary tract infection in a rabbit model. Am J Med. 1993; 94(3A):23S-30S.
61. Morck D W, Lam K, McKay S G, Olson M E, Prosser B, Ellis B D, et al. Comparative evaluation of fleroxacin, ampicillin, trimethoprimsulfamethoxazole, and gentamicin as treatments of catheter-associated urinary tract infection in a rabbit model. Int J Antimicrob Agents. 1994; 4 Suppl 2:S21-7.
62. Gottenbos B, van der Mei H C, Klatter F, Nieuwenhuis P, Busscher H J. In vitro and in vivo antimicrobial activity of covalently coupled quaternary ammonium silane coatings on silicone rubber. Biomaterials. 2002; 23(6):1417-23.
63. Costerton et al., *J. Bacteriol.* 176:2137-42, 1994.
64. Costerton et al., *Science* 284: 1318-22, 1999.
65. Arciola et al., *New Microbiol.* 22:337-41, 1999.
66. O'Gara and Humphreys, *J. Med. Microbiol.* 50:582-87, 2001.
67. Smrekar, F., M. Ciringer, M. Peterka, A. Podgornik, and A. Strancar. Journal of Chromatography B 861:177-180, 2008

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. Some publications are mentioned with a numeral enclosed in brackets and are directed to the relevant reference number presented in the enclosed Reference List. All patents and publications referred to herein are incorporated by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, define the scope of the invention.

The invention claimed is:

1. A medical device comprising:
one or more surfaces; and
a bioactive bacteriophage composition covalently tethered to a hydrogel coating material carried by one or more of said surfaces, wherein said bacteriophage are not embedded into said hydrogel coating material or said surface, and wherein the bacteriophage composition is capable of inhibiting formation of bacterial biofilm on the medical device.

2. The medical device of claim 1 wherein the bacteriophage composition is covalently tethered to the surface of said hydrogel coating material.

3. The medical device of claim 1 wherein the bacteriophage composition comprises a plurality of bacteriophage species, and the bacteriophage composition is capable of inhibiting the formation of a polymicrobic biofilm.

4. The medical device of claim 1 wherein the bacteriophage composition is tethered to the one or more surfaces of the device and said device has not been introduced into the body of a subject.

5. The medical device of claim 1 wherein the bacteriophage composition comprises an effective amount of divalent cations.

6. The medical device of claim 1 wherein the bacteriophage composition comprises $Ca^{2+}$, $Mg^{2+}$, or combinations thereof.

7. The medical device of claim 1 wherein the bacteriophage composition comprises a lytic bacteriophage composition.

8. The medical device of claim 1 wherein the bacteriophage composition comprises a *Ps. aeruginosa* bacteriophage composition, a *Pr. mirabilis* bacteriophage composition, or combinations thereof.

9. The medical device of claim 1 wherein the bacteriophage composition comprises a bacteriophage that inhibits the growth of bacteria of the family Enterobacteriacae.

10. The medical device of claim 1 wherein the bacteriophage composition comprises a bacteriophage that inhibits the growth of bacteria of a genus *Staphylococcus, Enterococcus, Pseudomonas, Proteus, Streptococcus, Citrobacter koseri, Enterobacter cloacae*, or combinations thereof.

11. The medical device of claim 1 wherein the bacteriophage composition comprises a bacteriophage that inhibits the growth of a bacteria that is *Staphylococcus aureus, Staphylococcus epidermidis*, coagulase-negative staphylococci, *Pseudomonas aeruginosa, Klebsiella pneumoniae, Escherichia coli, Enterococcus faecalis, Enterococcus faecium, Providencia stuarii, Proteus mirabilis, Morganella morganii, Acinetobacter calcoaceticus, Enterobacter aerogenes, Streptococcus agalactiae, Streptococcus avium, Streptococcus bovis, Streptococcus durans, Streptococcus faecalis, Streptococcus pneumoniae, Streptococcus suis, Streptococcus viridans*, bacterial pathogens that colonize tympanostomy tubes, prosthetic joints, central venous catheters, prosthetic heart valves, needleless connectors, or combinations thereof.

12. The medical device of claim 1 wherein said device is a bandage.

13. The medical device of claim 1 wherein the bacteriophage composition is capable of inhibiting biofilm formation for at least twenty-four hours.

14. The medical device of claim 1 wherein the device is sterile except for the bacteriophage composition.

15. The medical device of claim 1 wherein said surface is a polymeric material different from said hydrogel coating material.

16. The medical device of claim 1 wherein the device is a catheter, a stent, a shunt, an endotracheal tube, a gastric feeding tube, an artificial joint, an intrauterine device, an artificial voice prosthesis, a needleless connector for central venous catheters, a tympanostomy tube, an artificial heart valve, or a pacemaker.

17. The medical device of claim 1, wherein the bacteriophage composition, the surface, the coating material, or combinations thereof further comprises a surfactant, an antibacterial enzyme, an antibiotic, or combinations thereof.

18. The medical device of claim 1, wherein the bacteriophage composition or the surface further comprises an antibiotic.

19. The medical device of claim 18, wherein the antibiotic comprises a beta-lactam, a cephalosporin, an aminoglycoside, a sulfonamide, a macrolide, a tetracycline, a silver salt, or combinations thereof.

* * * * *